US008057390B2

(12) United States Patent
Witte et al.

(10) Patent No.: US 8,057,390 B2
(45) Date of Patent: Nov. 15, 2011

(54) HIGH-RESOLUTION MAPPING OF BIO-ELECTRIC FIELDS

(75) Inventors: Russell S. Witte, Tucson, AZ (US); Ragnar Olafsson, Ann Arbor, MI (US); Matthew O'Donnell, Seattle, WA (US)

(73) Assignee: The Regents of The University of Michigan, Ann Arbor, MI (US)

( * ) Notice: Subject to any disclaimer, the term of this patent is extended or adjusted under 35 U.S.C. 154(b) by 877 days.

(21) Appl. No.: 12/019,225

(22) Filed: Jan. 24, 2008

(65) Prior Publication Data
US 2008/0183076 A1    Jul. 31, 2008

Related U.S. Application Data

(60) Provisional application No. 60/897,849, filed on Jan. 26, 2007.

(51) Int. Cl.
*A61B 8/00* (2006.01)
*A61B 8/14* (2006.01)
*A61B 5/04* (2006.01)

(52) U.S. Cl. ........ 600/438; 600/459; 600/509; 600/544; 600/546

(58) Field of Classification Search .................. 600/437, 600/438, 509, 442, 450, 459, 508, 544, 546
See application file for complete search history.

(56) References Cited

U.S. PATENT DOCUMENTS
6,584,345 B2 * 6/2003 Govari ........................ 600/509
2007/0299353 A1 * 12/2007 Harlev et al. ................ 600/509

OTHER PUBLICATIONS

Olafsson et al., "Electric Current Mapping using the Acousto-Electric Effect", Proc. of SPIE, vol. 6147, Mar. 2006, pp. 1-11.*
Zhang et al., "Acousto-electric Tomography", Proceedings of SPIE, vol. 5320, Bellingham, WA, 2004.*

* cited by examiner

*Primary Examiner* — Long V Le
*Assistant Examiner* — Katherine Fernandez
(74) *Attorney, Agent, or Firm* — Harness, Dickey & Pierce, P.L.C.

(57) ABSTRACT

A current source density mapping system includes an ultrasound transducer emitting an ultrasound wave traveling along an ultrasound beam directed at a mapping field in a region of living tissue and an ultrasound pulser delivering a transmit pulse to said ultrasound transducer. The system includes a timing device producing controlled excitation of the transmit pulse; a plurality of recording electrodes positioned in contact with the living tissue detecting an acoustoelectric voltage signal generated at a bioelectric current source and within a focal zone of said ultrasound beam. An amplifier operatively connected to the recording electrodes amplifying the acoustoelectric voltage signal at a predetermined gain; and an analyzing component comprising a digitizer, a sampling device, a signal processor and a display unit operatively connected to the amplifier determining the location of the bioelectric current source by analyzing the acoustoelectric voltage signal detected by the recording electrodes in response to an interaction between the ultrasound wave and the presence of a current source in the mapping field.

20 Claims, 9 Drawing Sheets

HIGH-RESOLUTION MAPPING OF BIO-ELECTRIC FIELDS

CROSS-REFERENCE TO RELATED APPLICATIONS

This application claims the benefit of U.S. Provisional Application No. 60/897,849 filed on Jan. 26, 2007. The disclosure of the above application is incorporated herein by reference.

GOVERNMENT RIGHTS

This disclosure was made with government support under National Institutes of Health Grant Nos. EB003451, HL067647 and DE007057. The Government has certain rights in the invention.

FIELD

The present disclosure relates to systems and methods of mapping current fields in biological tissue based on the acoustoelectric effect (AEE) and lead field theory for non-invasive mapping of 2-D or 3-D current distributions.

BACKGROUND

The statements in this section merely provide background information related to the present disclosure and may not constitute prior art.

Approximately 100,000 of the 2.5 million people in the United States who suffer from epilepsy are serious candidates for surgical treatment. Interventional neurosurgery usually requires laborious, invasive pinpoint mapping of cortical function (local field and action potentials) to distinguish eloquent from dormant brain tissue prior to resection. Whereas EEG recording from many electrodes (>100) on the skull generally provides poor spatial resolution (>1 cm) of synchronous neural activity, subdural and depth electrodes dramatically improve spatial precision at the cost of invasiveness. Based on the acoustoelectric effect (AE effect or AEE), an interaction between local pressure and density, we assess whether ultrasound can be used to improve contrast and resolution of traditional electrical recording. This approach potentially improves spatial selectivity by reducing the source size to the position where only ultrasound and current wavefields intersect. An acoustic pressure wave P traveling in a biologic medium induces a local change in conductivity (given by $$d(\rho)/\rho = K_1(dP) \quad (1)$$

with K1 an interaction constant on the order of 0.01-0.1% per MPa in physiologic saline [2,3]. When P intersects a current field i in a uniform conducting medium, the change in conductivity leads to a voltage modulation V between two recording electrodes of resistance R0

$$V^{AE}(t) = K_2 i R_0 P(t) \quad (2)$$

Thus, the phase and magnitude of the induced AE voltage is proportional to the ultrasound pressure and applied current. Jossinet et al. have provided a more complete analysis of the AEE in an electrolyte solution. Although AEE was first reported by Fox et al. and was initially used to characterize colloids in solution, others have recently proposed applications of AE to medicine and biology. For example, acoustoelectric tomography has been proposed for high resolution electrical impedance imaging of breast tissue. The present disclosure relates to a system capable of measuring $V^{AE}(t)$ in an electrically active living tissue environment that reflects the applied passive current and pressure fields. A need therefore exists to develop sensitive methods to characterize and map electrical current in living electrically active tissue and provide additional spatial resolution using a minimally invasive technique that is cost effective over the existing electrical current mapping technologies.

SUMMARY

In some embodiments, a current source density mapping system in accordance with the present disclosure includes an ultrasound transducer emitting an ultrasound wave traveling along an ultrasound beam directed at a mapping field in a region of living tissue and an ultrasound pulser delivering a transmit pulse to said ultrasound transducer. The system includes a timing device for producing controlled excitation of the transmit pulse; a plurality of recording electrodes positioned in contact with the living tissue operable to detect an acousticelectric voltage signal generated at a bioelectric current source and within a focal zone of said ultrasound beam. An amplifier operatively connected to the recording electrodes amplifying the acoustoelectric voltage signal at a predetermined gain; and an analyzing component comprising a digitizer, a sampling device, a signal processor and a display unit operatively connected to the amplifier, to determine the location of the bioelectric current source by analyzing the acoustoelectric voltage signal detected by the recording electrodes in response to an interaction between the ultrasound wave and the presence of a current source in the mapping field.

Methods are also provided to use the current source density mapping system to image and map in 2-D and 3-D detailed current source densities of living tissue being interrogated within a mapping field. The method comprises placing a two or more recording electrodes within a mapping field and substantially near or in contact with a living tissue having a current source in the path of a current field. The recording electrodes detect a voltage signal. The ultrasound beam can be directed to at least one position in the mapping field such that the ultrasound transducer transmits an ultrasound wave to the position in the mapping field. The voltage signal can be measured at the position comprising an acousticelectric voltage signal produced at a position located at an intersection between a focal zone of the ultrasound beam and said current source through the plurality of recording electrodes. The received acoustoelectric voltage signal is processed to derive position data of the current source, the data comprising data points, each data point comprising a magnitude of the current source sampled at the position relative to the mapping field in the living tissue. The resultant position data can be stored in memory. The data points stored in the memory are converted to an image representing a density of current within at least a portion of the mapping field and then displaying the image on a display.

DRAWINGS

The drawings described herein are for illustration purposes only and are not intended to limit the scope of the present disclosure in any way.

Figure 4A:
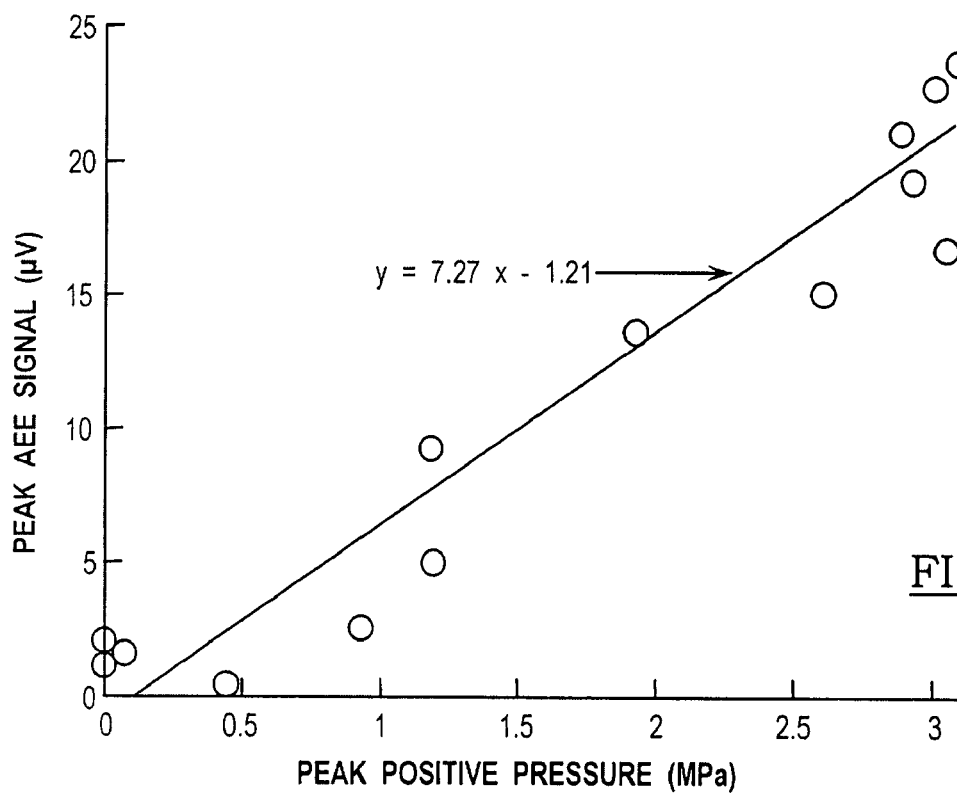

FIG. 4A is a graphical representation illustrating an AEE signal amplitude as a function of peak positive pressure. The empty circles are data points and the solid red line is a linear fit. The current injection is 50 mA (~8 mA/cm$^2$) sinusoidal current in accordance to the present disclosure.

Figure 4B:
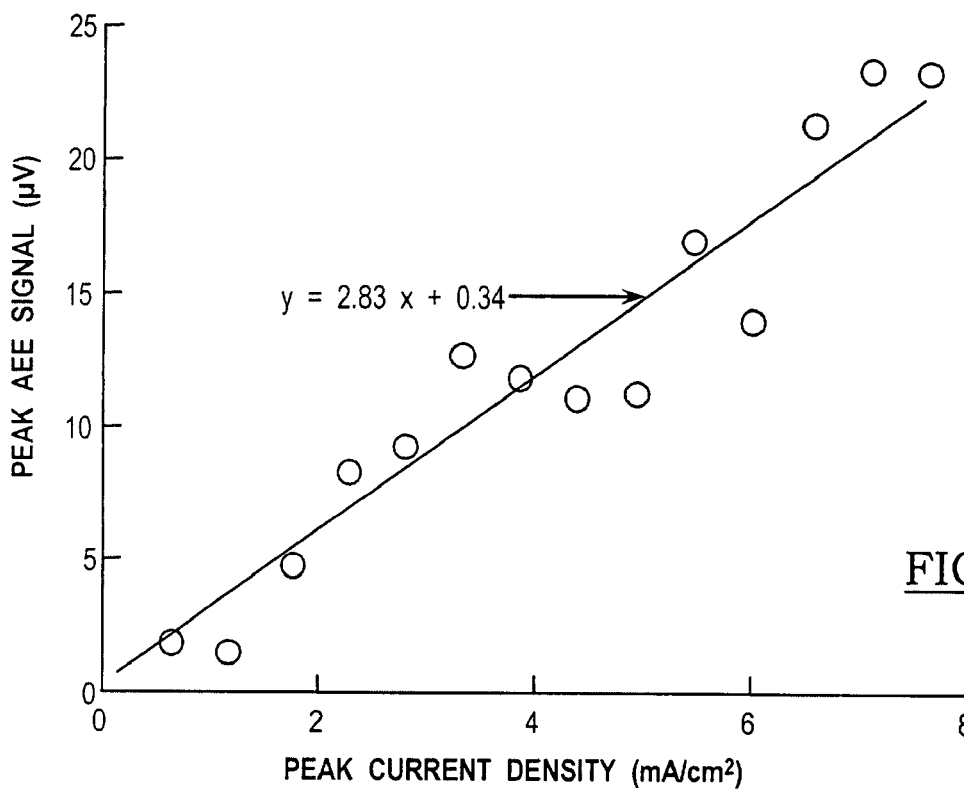

FIG. 4B is a graphical representation illustrating an AEE signal amplitude as a function of injected sinusoidal current. The empty circles are the data points and the solid red line is a linear fit. The peak positive pressure used was 3 MPa in accordance to the present disclosure.

Figure 5:
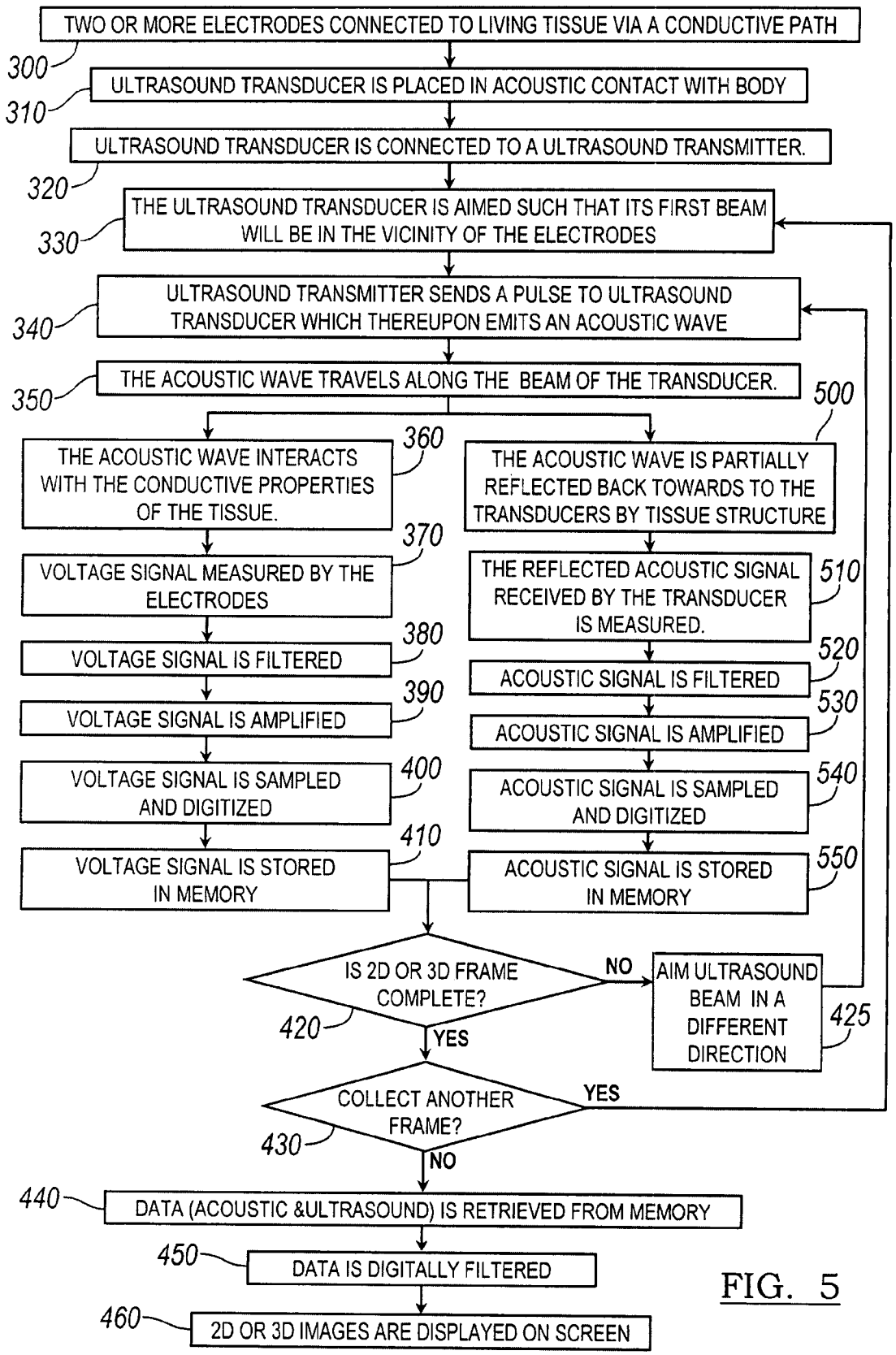

FIG. 5 is a block diagram of a method used to calculate and map the current source density of the living tissue optionally showing a method of co-regestering a pulse echo image in accordance to the present disclosure.

Figure 6:
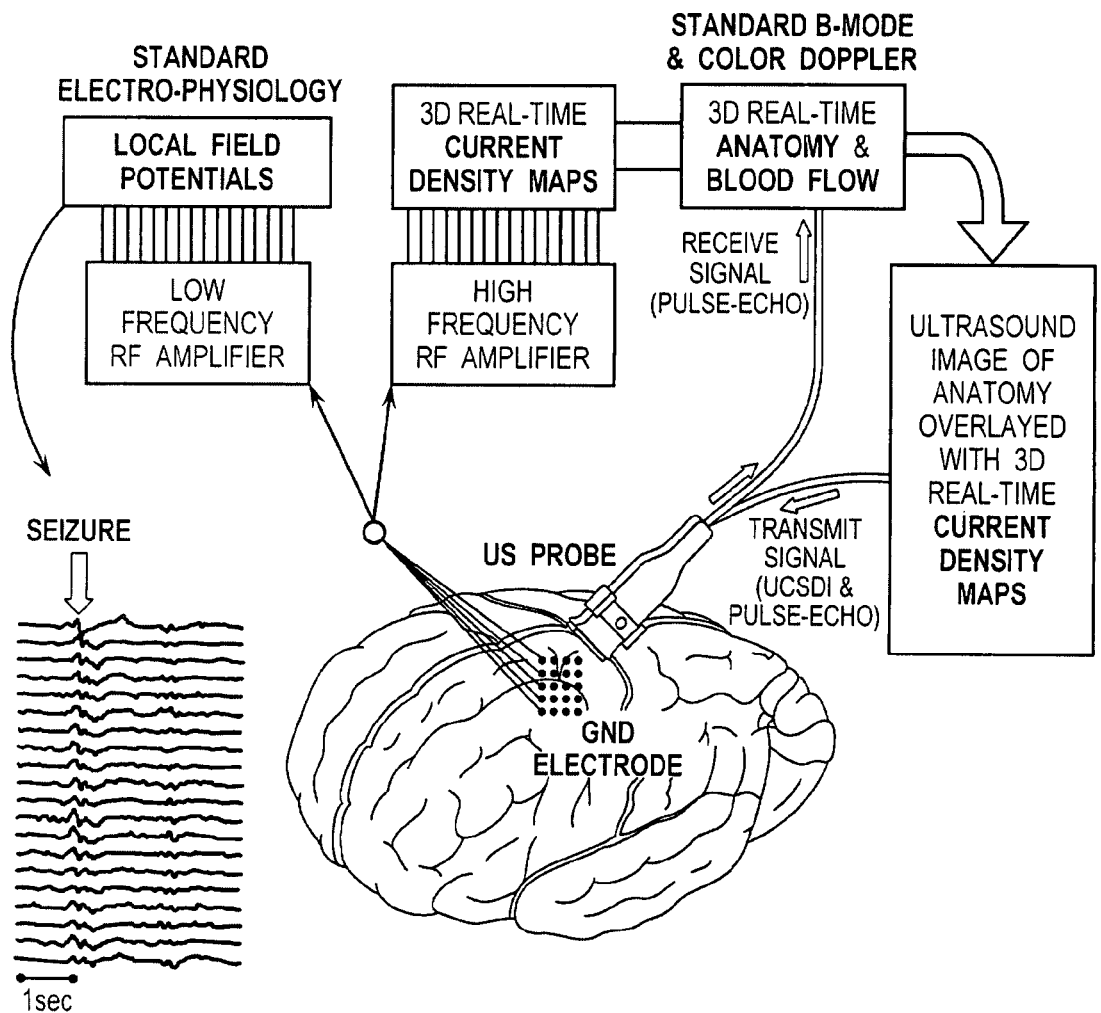

FIG. 6 is an illustration and method showing a multimodal imaging system adapted for the system that allows for traditional electrophysiology, anatomical ultrasound imaging (pulse-echo), blood flow imaging (Color Doppler) and current source density maps in accordance to the present disclosure.

Figure 7B:
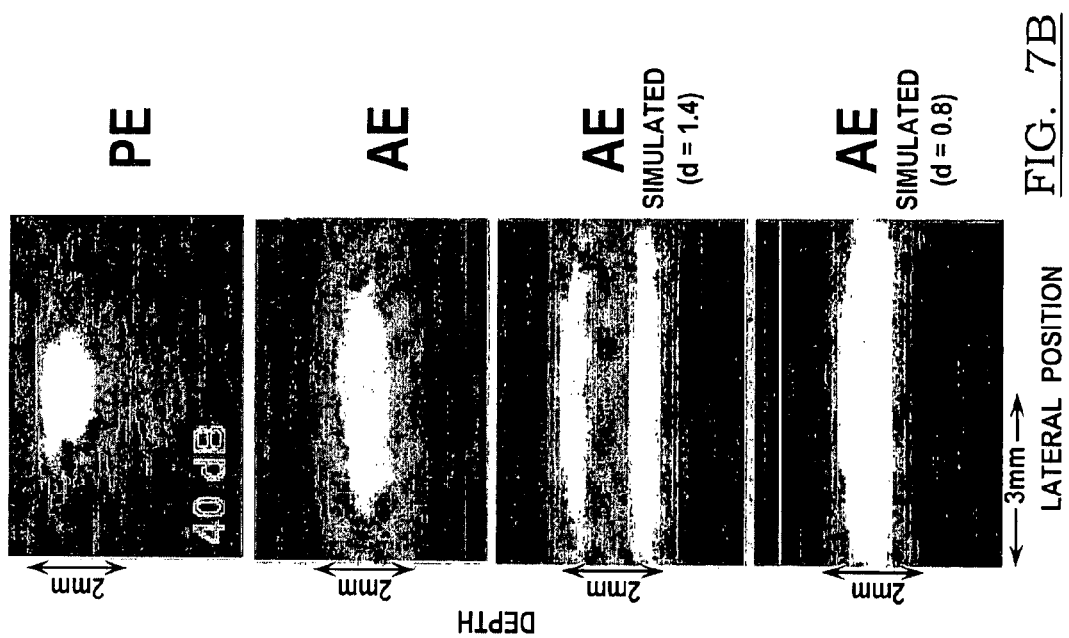
Figure 7A:
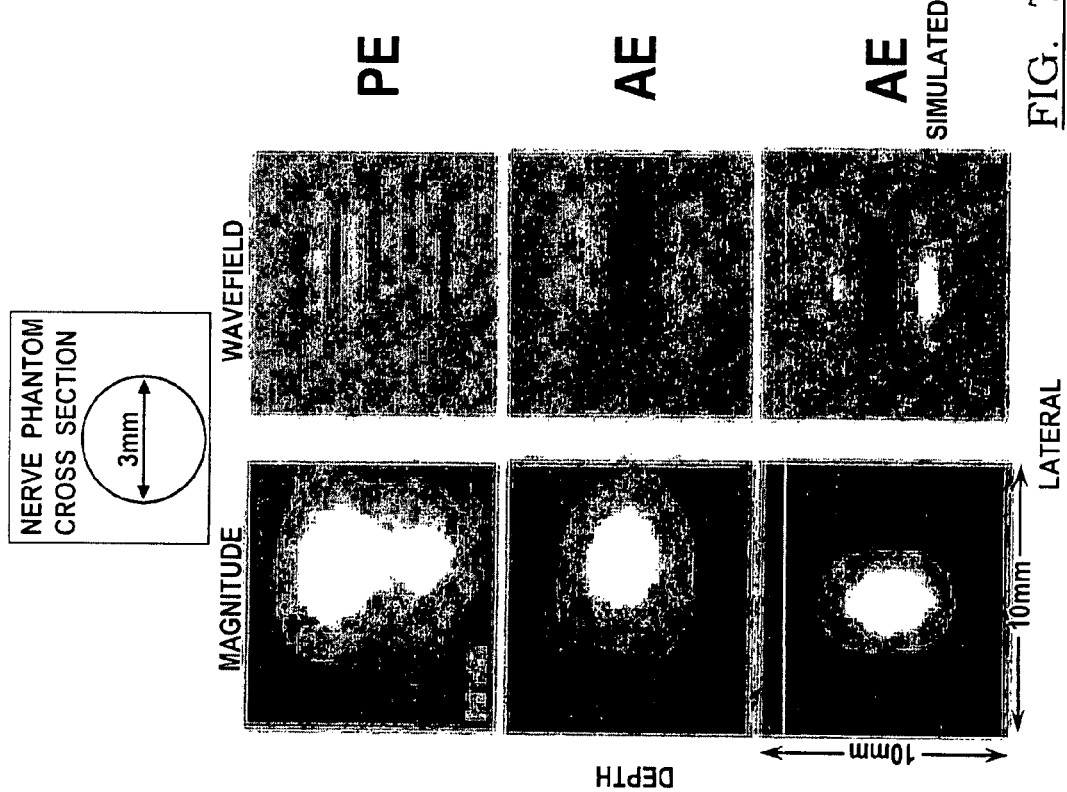

FIG. 7A is a cross-sectional scan of a nerve phantom produced as a 2-D image in accordance with the present disclosure.

FIG. 7B is a depiction of the pulse echo images when an abdominal nerve cord is pulsed with a 7.5 MHz ultrasound transducer wherein the diameter of the cord is less than 2 mm. The PE and AE is obtained using a current density of 80 mA/cm$^2$. Dynamic ranges for the plots are 40 dB for the pulse echo and 20 dB for the AE image.

Figure 8A:
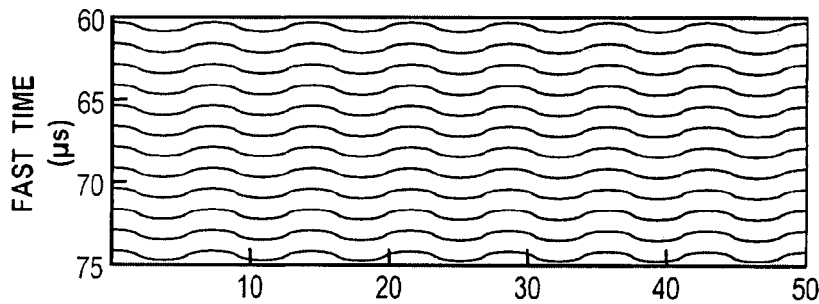

FIG. 8A is a graphical representation illustrating a wavefield of the signal, that is the difference between the waveform recorded at 8 mA/cm$^2$ and the waveform recorded at 0 mA/cm$^2$) in accordance with the present disclosure.

Figure 8B:
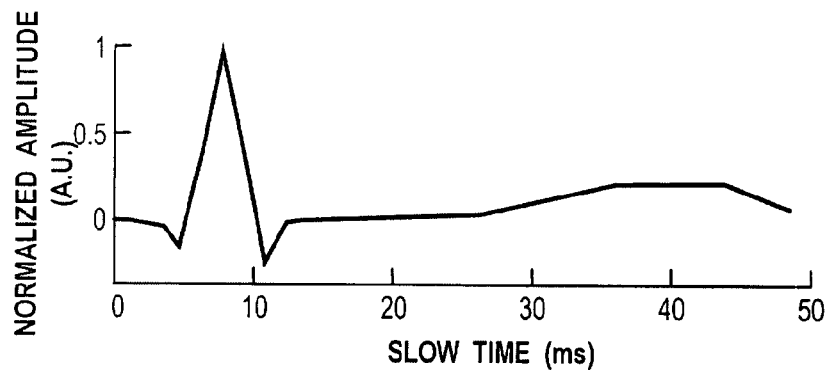

FIG. 8B is a graphical representation illustrating the signal of the current generator in accordance to the present disclosure.

Figure 8C:
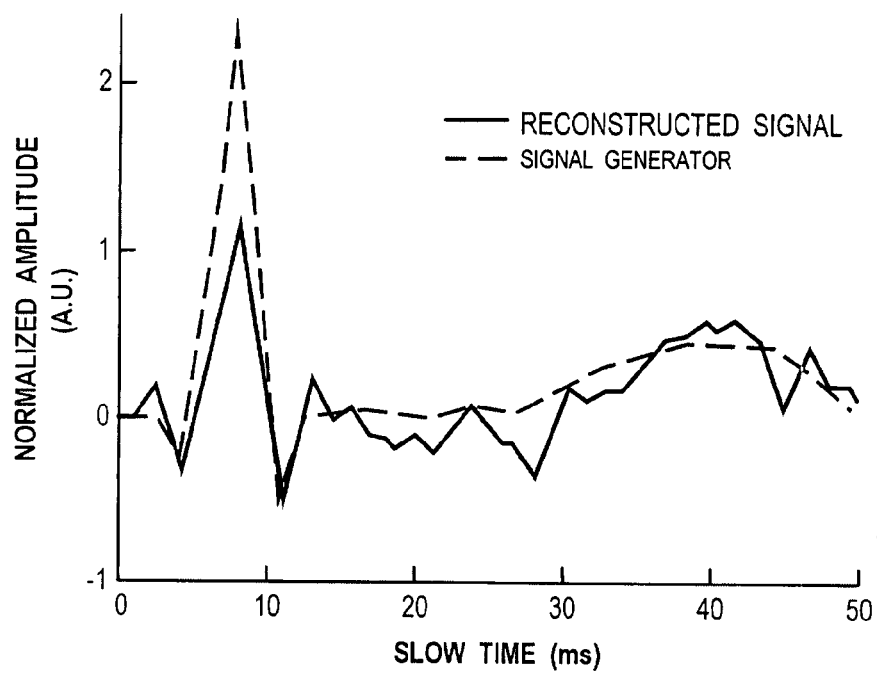

FIG. 8C is a graphical representation illustrating a dotted line with the ECG waveform recorded directly from a signal generator and a blue solid line with the low frequency waveform reconstructed from the wavefield between 60 μs and 70 μs shown in accordance with the present disclosure.

Figure 9A:
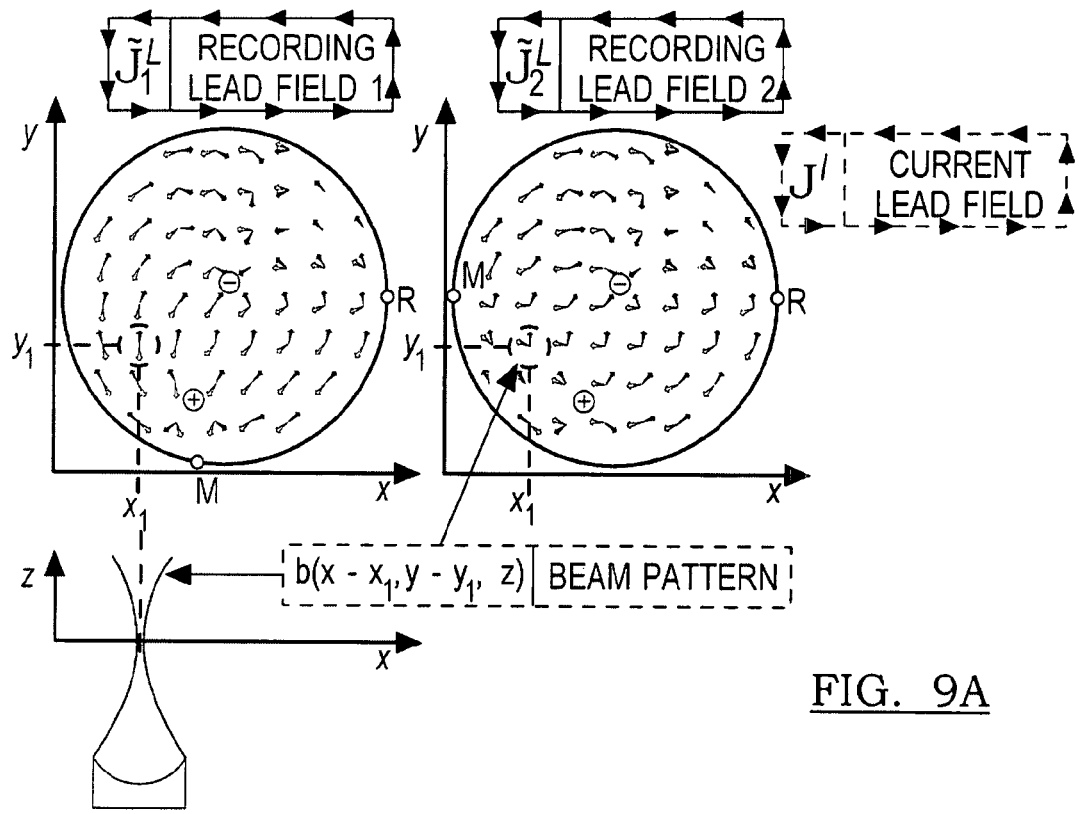

FIG. 9A is a graphical representation illustrating of the different factors in equation (8), the AE signal equation, as well as the sifting property of the ultrasound beam, the basis for the reconstruction algorithm method in accordance to the present disclosure.

Figure 9B:
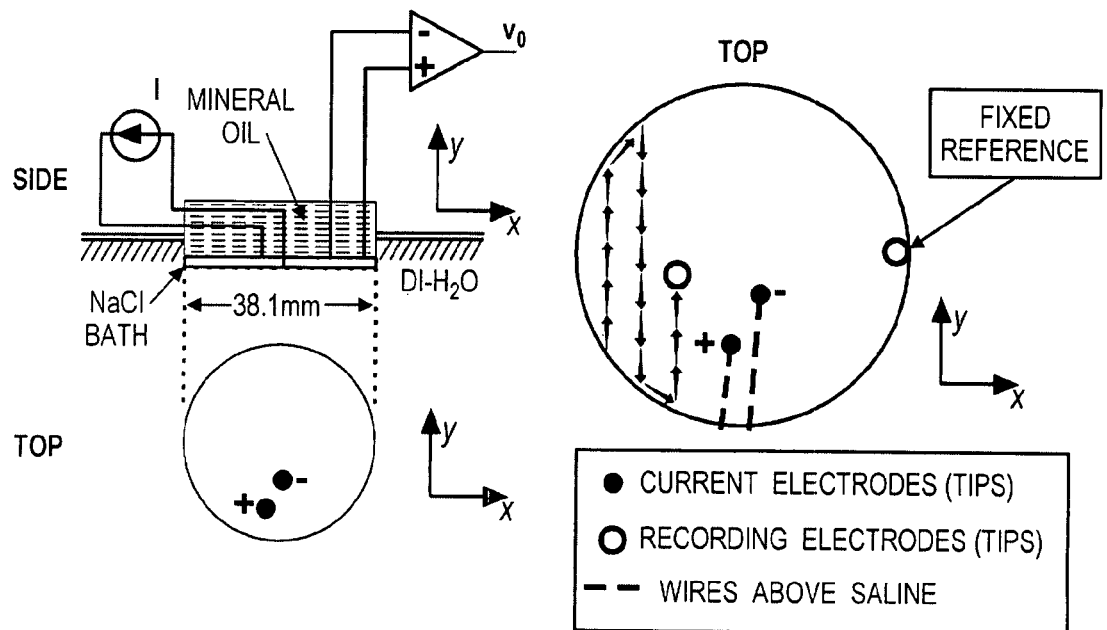

FIG. 9B is a graphical representation illustrating experimental setup for conventional low frequency measurement. A current distribution was generated by injecting current I through two AgCl electrodes "+" and "−" into a 1-mm thick 0.9% NaCl saline bath.

DETAILED DESCRIPTION

The following description is merely exemplary in nature and is not intended to limit the present disclosure, application, or uses.

In some embodiments, a method based on the acoustoelectric effect (AEE) and lead field theory can be performed for non-invasive or invasive mapping of 2-D or 3-D current distributions. The AEE is a pressure-induced conductivity modulation, in which focused ultrasound can be used as a spatially localized pressure source. When an ultrasound beam is focused between or in the vicinity of a pair of recording electrodes, a voltage will be induced due to the pressure-modulated conductivity change and the local current density. In some embodiments, the procedure for mapping and imaging the location and/or orientation of current sources in living tissue has been referred to herein as ultrasound current source density imaging (UCSDI).

Figure 1A:
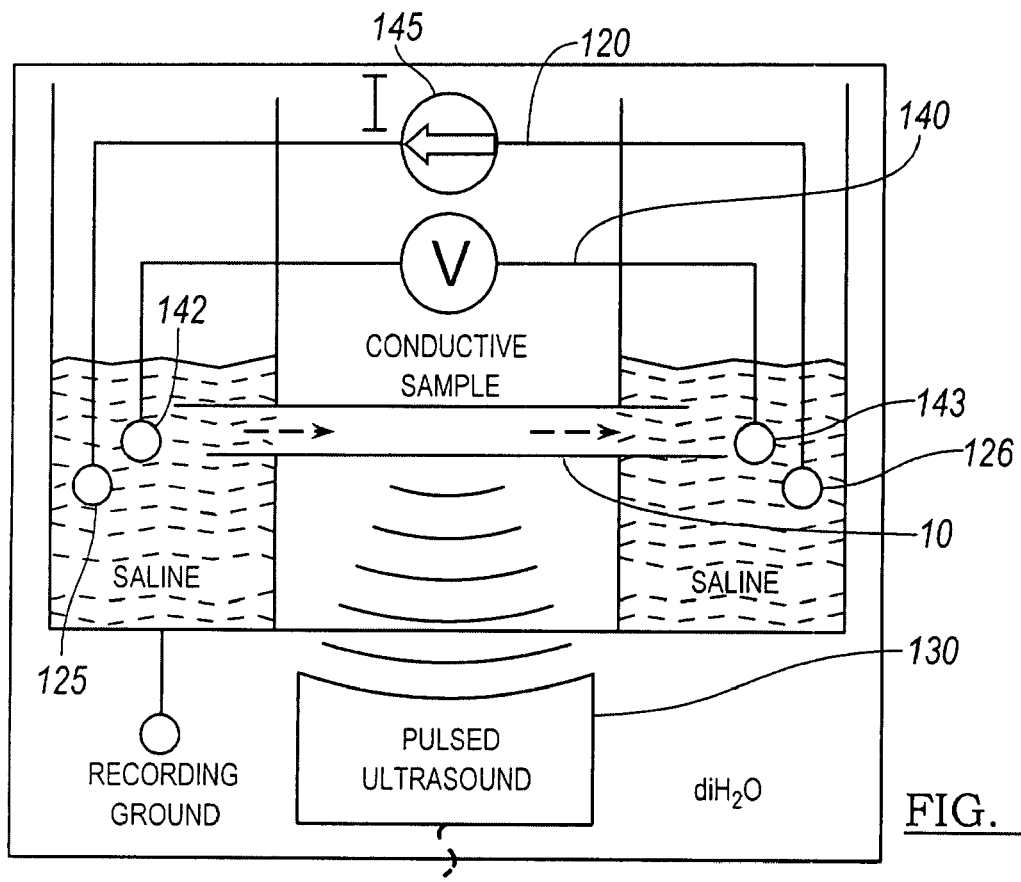
FIG. 1A is an illustration of a 3 compartment neural recording chamber representative of a current source density mapping system used to detect an AE signal in a phantom where the living tissue is mimicking a nerve structure in accordance with the present disclosure.
Figure 1B:
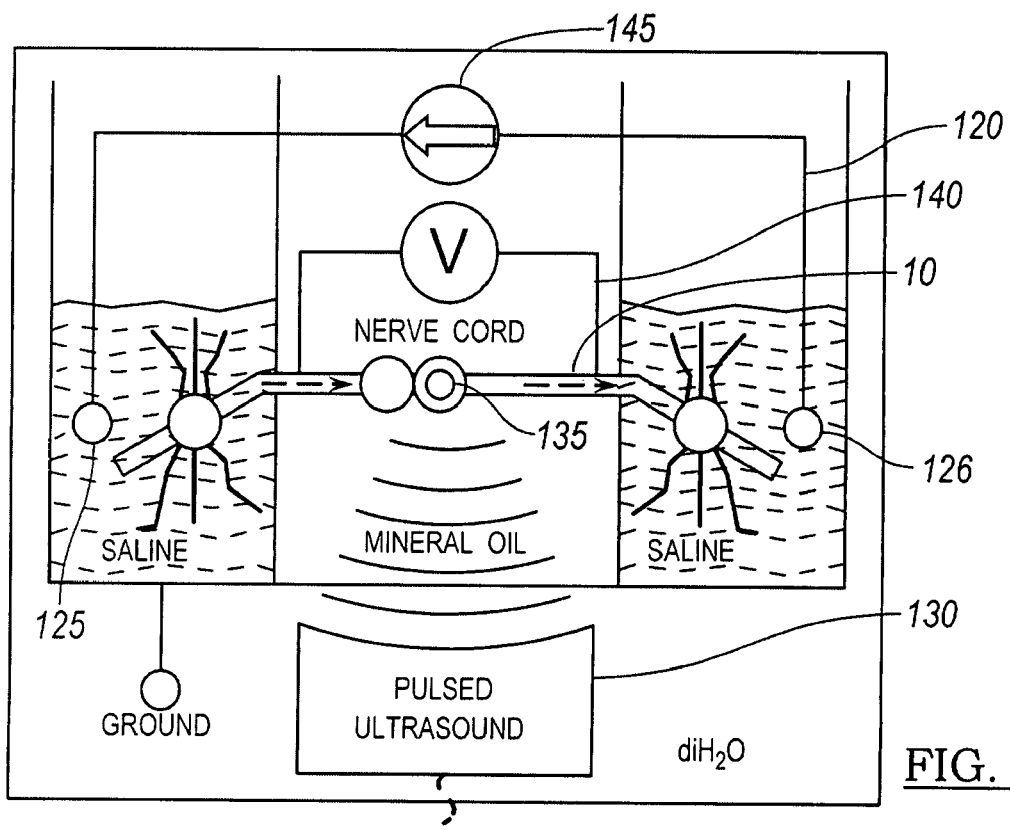
FIG. 1B is an illustration of a 3 compartment neural recording chamber representative of a current source density mapping system used to detect an AE signal in a 3 compartment current source density mapping system used to detect an AE signal in a lobster nerve cord in accordance with the present disclosure.

FIGS. 1A & 1B illustrate a basic representations of some embodiments of the present disclosure for measuring the current source density in an electrically conductive living tissue and experimental phantom mockups. A beam of pulsed ultrasound produced by an ultrasound transducer 130 is focused on or into a living tissue 10. In some embodiments described throughout the present disclosure, a living tissue 10 can be any biological tissue or cells, cellular components, or groups of cells that are capable of transmitting electrical current. In other words, the living tissue 10 can be any electrically active tissue, cells, cellular components and groups of cells, including for example, a neuron, a foci of neurons, nerve fibers, nerve cords, spinal tissue, brain tissue, myocytes, cardiomyocytes, muscle fibers, cardiac tissue, skeletal muscle, cell membranes, micelles, artificial membranes and ion channels.

The living tissue 10 is disposed between or located in the vicinity of a plurality, (two or more) recording electrodes 142 and 143 which form a circuit 140. In some embodiments, the plurality of recording electrodes 142 and 143 can include: a pair of single electrodes, grid electrodes, depth electrodes, electrode arrays and combinations thereof. In some embodiments, the electrodes can comprise a conducting metallic material, such as biocompatible conductive metals, including, for example, tungsten, silver, silver chloride, gold, platinum, iridium, titanium, platinum alloys, iridium alloys, or titanium alloys. In some embodiments, at least one of the recording electrodes 142 and 143 can be a component of a surgical device, for example a catheter, a laparoscopic device, a lead wire, an electrode probe, a navigation probe and the like. In some embodiments, the recording electrodes 142, and 143 can be a component of a specialized mapping device pertaining to neural or cardiac mapping, for example a catheter having an array of electrodes, for example, a basket electrode catheter described in U.S. Pat. No. 7,149,563 which is hereby incorporated in its entirety.

In some embodiments, the mapping system of the present disclosure can optionally include a current generator as shown as current generator 120, having an ammeter 145. The current generator 120 is optionally included when an extraneous current for example a controlled low frequency AC current is introduced to the living tissue 10. In some embodiments, the current generator 120 can comprise a plurality of electrodes 125 and 126 in electrical communication with the current generator that are positioned in contact with the living tissue 10 or in the vicinity of living tissue 10, sufficiently close to enable a current to propagate and be detectable by the recording electrodes 142 and 143. The current generator 120 can also include a power source in electrical communication with current generator 120 and electrodes 125 and 126. Typically, a low frequency AC voltage is applied across electrodes 125 and 126 of 50-250 Hz with a current of 5-200 mA. The current generated within the living tissue depends on the tissue being mapped (for example a higher current is generated in cardiac tissue as opposed to neuronal tissue), the spatial arrangement of the electrodes 125 and 126 in relation to the living tissue 10 and the density and conductivity of the living tissue 10 being mapped.

As shown in FIG. 1B, an embodiment of the present disclosure is illustrated using living tissue 10 e.g. a nerve cord derived from fresh lobster as an example of an electrically conductive living tissue. The apparatus set up for mapping current sources propagated through the living tissue 10 is the same as shown in FIG. 1A. The current generator 120 was used to deliver passive current at 300 Hz. Recording electrodes 142 and 143 (not shown) are coupled to the living tissue 10 to form a circuit 140. In some embodiments, the ultrasound transducer 130 used to produce the ultrasound beam can include single and dual-element ultrasound transducers with center frequencies ranging from 0.1 to 3100 MHz, focal pressures up to at least 2.0 MPa, focal lengths between 10 mm and 500 mm and f/# between 1 and 5.

In some embodiments of the present disclosure a system for mapping current sources and biopotentials are disclosed. The AE signal is only generated at the position or intersection where the ultrasonic wave's focal zone intersects a bioelectric current source. The magnitude of the AE signal is proportional to the current density of the current source. The spatial resolution of the present technology employing ultrasound transducers producing a tightly focused high-frequency (50-100 MHz) beam could be as low as 15-30 μm and the sensitivity of present technology as low as 1 mA/cm$^2$. The present disclosure provides for current source mapping and imaging that is mostly independent of the distribution of the tissue resistivity as found in biopotential mapping using electrode arrays, including catheters. In some embodiments, the ultrasound transducer 130 can be raster scanned at the minimum in the XY, planes to generate 3-D data of current densities in living tissue 10. In some embodiments, the ultrasound transducer 130 can be mounted on a mechanical stage or, alternatively, the ultrasound beam can be electronically steered as commonly done with synthetic aperture ultrasound arrays (or commonly done with commercial ultrasound scanners), such that the current source location, defined by the ultrasound focus, can be determined in 2-D or 3-D and can be automatically co-registered with position data obtained from existing surgical navigation systems, for example magnetic, MRI, X-Ray, CT, optical and ultrasound navigational positioning systems. In some embodiments, the position and orientation of a current source in living tissue 10 can be determined with pulse-echo ultrasound imaging of the living tissue co-registered with the AE signal ($V^{AE}$) at any given position. Such spatial sensitivity, 3-D capability, indifference to tissue resistivity and other advantages described herein, provide for a sensitive and detailed mapping and imaging modality for ultrasound current source density mapping based on the acoustoelectric signals generated by living tissues in real-time.

Figure 2:
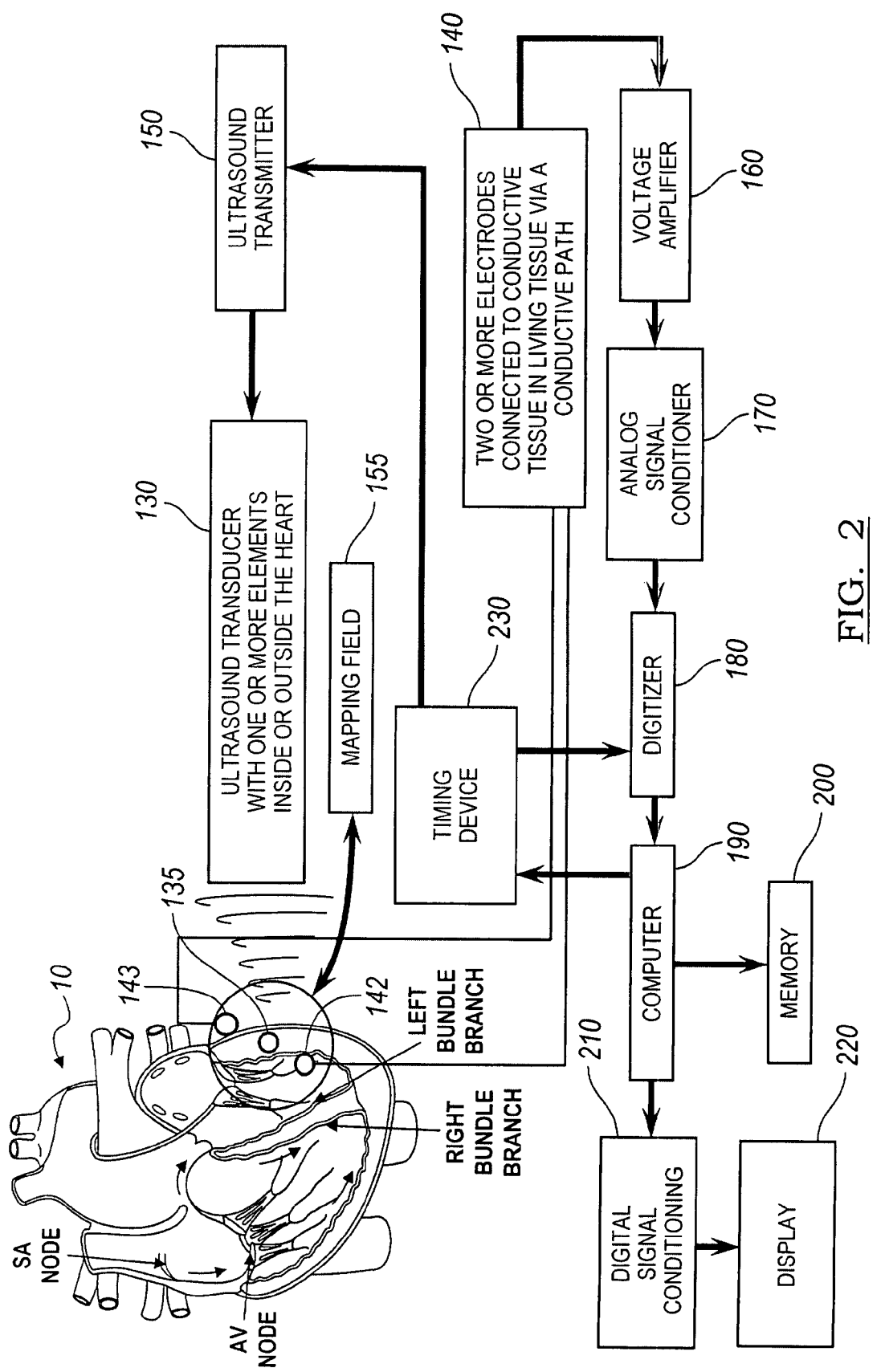
FIG. 2 is a block diagram of a current source density mapping system in accordance to the present disclosure.

As illustrated in FIG. 2, a current source mapping and imaging system comprises an ultrasound transducer 130 positioned either outside of the living tissue 10 as shown, or optionally, the transducer may be operable from within the subject, interrogating the living tissue 10 from within the subject. In some embodiments, the ultrasound transducer 130 or one or more of its elements, may form part of a catheter or other surgical device that is operable to transmit ultrasonic waves from within the heart, muscle, brain, spinal cord and the like. In some embodiments, the ultrasound transducer 130 is positioned outside of the patient or subject and producing a focal zone 135 in a living tissue within the patient or subject. In some embodiments, the ultrasound transducer 130 can be pulsed from 1 to 512 times at any of the current waveform at a single location in the living tissue 10 or pulsed 1 to 512 times at any time point of the current waveform at a plurality of locations in the living tissue 10. The AE signals produced at the plurality of locations can be used to generate 2-D and 3-D current source or density maps of living tissue 10.

In some embodiments, the ultrasound transducer 130 can be provided to deliver pulses of ultrasonic waves travelling along the axis of the ultrasound beam and is directed to one or more positions within a mapping field. The ultrasound transducer 130 can have a focal beam width ranging from about 50 μm to about 20 mm, or from about 2 mm to about 15 mm, or from about 3 mm to about 10 mm, or at least about 5 mm wide. In some embodiments, the ultrasound transducer 130 produces an ultrasound beam capable of producing a focal length ranging from about 1 mm to about 500 mm, or from about 10 mm to about 250 mm, or from about 20 mm to about 200 mm or a focal length of at least 50 mm. The ultrasound transducer can have center frequencies ranging from about 100 kHz to about 300 MHz. The ultrasound transducer is pulsed by an ultrasound transmitter 150, which sends signals to the ultrasound transducer 130 to pulse at controlled intervals. In some embodiments, the ultrasound transducer 130 can be triggered with a signal from the ultrasound transmitter 150 to coincide with any point on a current waveform propagating through the living tissue 10. In some embodiments the ultrasound transmitter is operable to transmit pulsed sequences and coded pulse sequences including for example chirp pulsed sequences, Barker or Golay coded pulses. In some embodiments, the ultrasound transmitter can include a GE Panametrics 5077PR squarewave pulse/receiver (GE Panametrics, Williston, Vt. USA). The ultrasound transmitter receives its timing queues from a timing device 230 which is operatively connected to a computer 190 for sequencing the proper current waveforms. In some embodiments, timing device 230 can also optionally include a trigger control instrument synchronized to a master clock. The timing device 230 is operable to produce controlled excitation of a transmit pulse that is sent to the ultrasound transducer 130. The master clock can be synchronized with either a field-programmable gate array (FPGA), programmable logic array and integrated circuits commonly used in electrical timing controllers. The computed propagating current waveform propagating through the living tissue 10 can be determined using a computer and the timing queue sent to the FPGA. In some embodiments, FPGA then issues a trigger to the ultrasound transmitter 150 after a predetermined delay.

In some embodiments the ultrasound transducer can be operated to manually or automatically scan and send an ultrasound beam to the living tissue 10 at positions of current flow thereby generating the acoustoelectric voltage signal without physically moving the ultrasound transducer or any of its elements. In addition, further scanning of the living tissue 10 can be made when the ultrasound transducer 130 is mounted on a mechanical translation stage or when its beam is electronically steered or if the ultrasound transducer 130 is part of a navigable catheter, lead or surgical probe. The mechanical stage can automatically and precisely orient the ultrasound transducer 130 around the living tissue to control the placement of the ultrasound beam and ultrasound wave within the mapping field or the beam of the ultrasound transducer 130 can be electronically steered to control the placement of the ultrasound beam and ultrasound wave within the mapping field. Ultrasound transducer 130 then sends one or more beams per millisecond along a beam axis to one or more positions in the mapping field 155 of the living tissue 10. The $V^{AE}$ signal whose magnitude is representative of the current density will only be detected where the focal zone of the ultrasound beam intersects the current field. By positioning at least one of the plurality of recording electrodes 142 and 143 within the mapping field 155 in contact with the living tissue or in the vicinity of the current source being measured, a circuit 140 can be made to detect voltage that comprises high frequency $V^{AE}$ signal and a low frequency $V^{LF}$ signal representative of the dipole current field. The $V^{AE}$ signal is then amplified by a voltage amplifier. The voltage amplifier 160 can be a differential voltage amplifier stage, or an oscilloscope (LeCroy, Inc. Chestnut Ridge, N.Y. USA) used to amplify the $V^{AE}$ signal with a gain of 10-200 dB. In some embodiments, when the ultrasound beam is used to generate the pulse-echo signal, the resulting pulse-echo signal is received by the ultrasound receiver (not shown).

The voltage amplifier 160 sends the resulting signal to an analog signal conditioner 170. The analog signal conditioner 170 can be a voltage filtering system comprising a high pass filter and optionally a low pass filter operably connected to the circuit 140. The analog signal conditioner 170 can be designed to separate the high frequency $V^{AE}$ signals (greater than approximately 100 kHz) from the low frequency $V^{LF}$ signals (less than approximately 100 kHz) present in the recorded voltage obtained by the circuit 140.

In some embodiments, the resultant $V^{AE}$ signal can be further analyzed with an analyzing component comprising an analog signal conditioner 170, a digitizer 180, a signal conditioning device 210, a computer 190 and a display 220. As used herein the signal conditioners, 170 and 210 can also include a sample device. In some embodiments, the $V^{AE}$ signal can be amplified in the analog signal conditioner 170 and passed on to a digitizer 180. Digitizer 180 converts normally analog type signals into coded binary data and transmits the resulting digital measurement signal to a computer 190. In some embodiments, the functions of the voltage amplifier 160, analog signal conditioner 170 and digitizer 180 can be produced using one, or two or three devices. For example, the voltage amplifier 160 and analog signal conditioner 170 can be integrated parts of an oscilloscope. Other multifunctional electrical signal processing devices may include one or more parts of voltage amplifier 160, analog signal conditioner 170 and digitizer 180 in one housing.

The computer 190 can comprise a central processing unit, a graphics card, random access memory 200 and one or more software applications stored in said memory 200 for computation of $V^{AE}$ signal and for mapping said $V^{AE}$ signal for display. The frame rate of the imaging system is determined by the pulse repetition rate of the ultrasound transducer, which can exceed 10 kHz. The calculation and manipulation of the $V^{AE}$ signal can be performed using Matlab™ (Natick, Mass. USA). Calculation of the ultrasonic field pressures can be performed using the ultrasound field simulation software Field II™ (http://www.es.oersted.dtu.dk/bme) and the like. Simulation of the current sources and electric lead fields can be performed on computer 190 using FEMLAB™ (Burlington, Mass. USA) or other finite element software.

Computer 190 is also connected to memory 200 and a digital signal conditioning device 210. Memory 200 can store acoustoelectric inputs described above including, for example, the high frequency $V^{AE}$ signal and low frequency $V^{LF}$ signals, the reconstruction algorithm data discussed below, and images produced by the navigation system to be co-registered with the current source density mapping, and the co-registered data. Output from the computer 190 comprising the current dipole field, and/or the pulse echo digitized images and the current source or density images can be fed into a digital signal conditioning device 210 and then displayed on display 220. As shown in FIG. 2, a representative current source density mapping system for a wide array of living tissues. More selective adjustment of electrode types, electrode placement and selection of transducer and ultrasound beam pressure can be tailored by the electrophysiologist/radiologist to enable the basic system of FIG. 2 to be implemented for different mapping applications. For example, although the living tissue 10 of FIG. 2 is represented as a heart, the same mapping system can be adopted for any electrically conductive tissue, cells, groups of cells, cellular components and the like.

Figure 3:
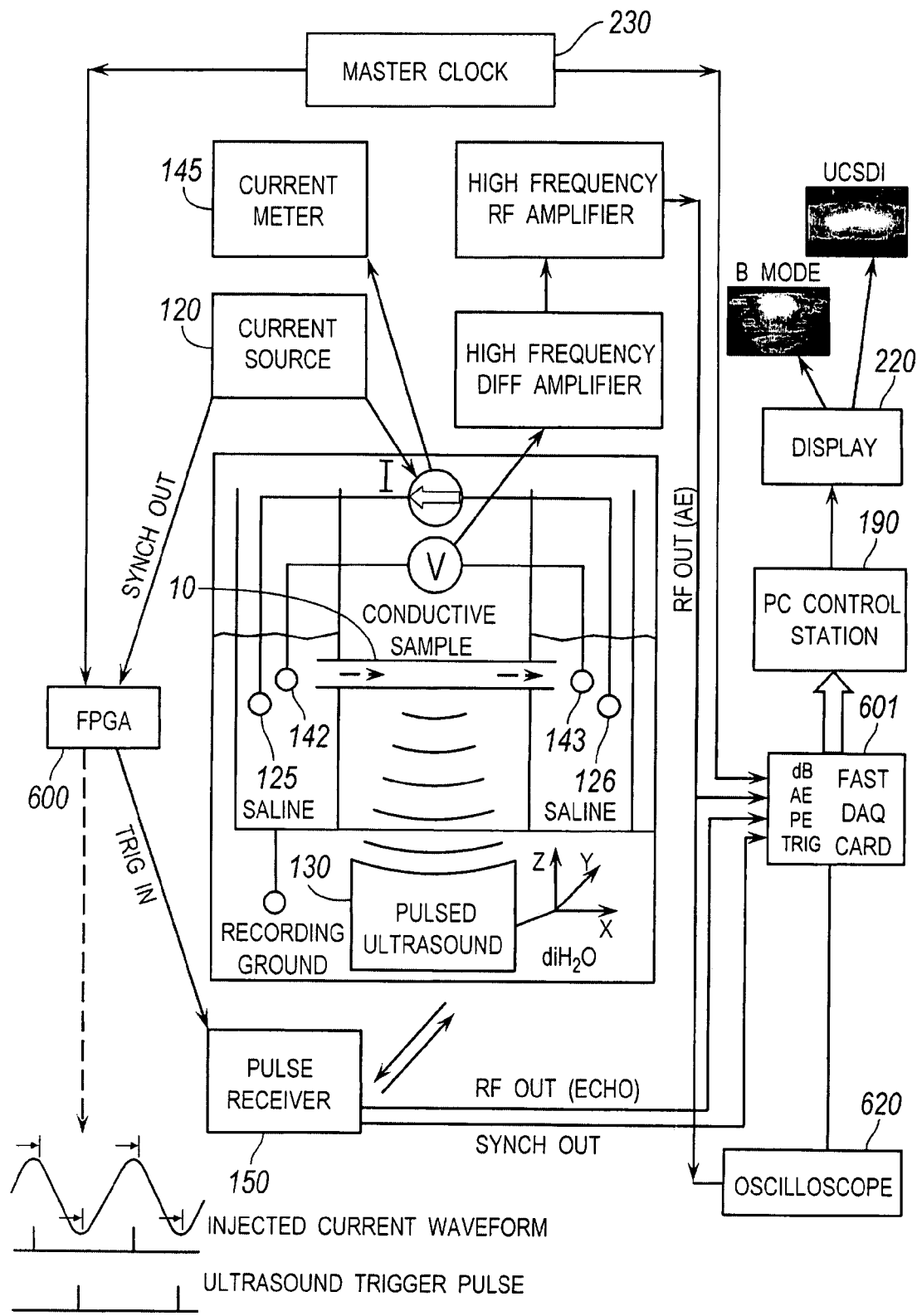
FIG. 3 is an illustration of a method for mapping current source density showing the basic components of the first combined pulse-echo and current source density imaging system in accordance to the present disclosure.

FIG. 3 shows in one embodiment, a system for mapping current in a nerve or for nervous, neuronal or other living tissue 10 that is connected with neurons or their cellular components. Typically, the current density of a small human neuron can range from less than approximately 0.1 mA/cm2 to approximately 10 mA/cm2 in the heart. An ultrasound transducer 130 sends an ultrasonic pulse to the living tissue 10. FIG. 3 also combines pulse-echo data showing structure and anatomy with current source density data to provide maps and images of current sources in a living nerve. Current flow was finely controlled by the amplitude of a current generator 120. AC current waveforms can be used to primarily reduce unwanted effects of direct current, such hydrolysis or polarization at the electrode interface. In some embodiments, the waveforms can be used when it is desirable to control the current density traveling through tissue. In live experiments, an external pulse could be optionally used instead of directly stimulate the said living tissue, causing a time-delay intrinsic propagation of electrical activity and current flow through the said tissue which could be mapped using the said technique. Current densities could be estimated from the cross sectional area of the living tissue 10 determined from co-registered pulse-echo images. In some embodiments, the current source density mapping system of the present disclosure can be adapted for diagnosing and treatment of epilepsy. The $V^{AE}$ signal can be generated using an ultrasound transducer 130 operatively connected to a ultrasound transmitter 150. Pulses are transmitted to the ultrasound transducer at a peak or trough of the current waveform generated by current generator 120. The current generator 120 can include a current generator (for example Model 33120A Agilent Inc. Santa Clara, Calif. USA) and produces a low frequency current between electrodes 125 and 126 (not shown). The signal generator or timing device 230 provides two signals used in the present disclosure. The first signal can be a 10 MHz signal to the field-programmable gate array (FPGA) 600. The second signal as shown in FIG. 3 can include a 100 MHz signal synchronized to digitizer 610. This signal serves as the base clock signal of the digitizer 610. The current source provides the timing of the ultrasound pulse/receiver via field-programmable gate array (FPGA) 600. In some embodiments, the FPGA is commercially available from Dallas Logic, Plano, Tex. USA. In some embodiments, the FPGA can include any commonly known hardware circuits such as ezFPGA circuit boards from Dallas Logic. The circuit boards can then be programmed with a timing program such as Quartus II software (Altera Corp. San Jose, Calif. USA). The living tissue 10 in FIG. 3 is a phantom conductive sample, but it can be replaced with any living tissue 10 including muscle fibers, nerves nerve cords, neural tissue, brain, spinal cord, cardiac tissue and the like.

Upon propagation of current from the current source through the electrodes 125 and 126 (not shown) the ultrasound pulse is beamed onto the living tissue 10, providing a focal zone of ultrasound pressure in the living tissue 10 that can be used to determine the current density at the intersection of the current source and ultrasound focal zone. The ultrasound produces a plurality of pulses to both the AC current maxima and minima and the voltage across electrodes 125 and 126 is obtained and amplified through high frequency differential amplifier 602 and filtered and amplified through high frequency RF amplifier 603. The $V^{AE}$ signal outputted from high frequency RF amplifier 603 can be processed using an oscilloscope and digitizer 620 and 610 respectively to sample and digitize the $V^{AE}$ signals. The high frequency signals collected by the digitizer 610 commercially available as PDA12 (Signatec, Inc. Newport Beach, Calif. USA). The digitizer 610 has two data channels, one trigger channel and one clock input. In some embodiments, the 100 MHz master clock 2230 signal generator is fed into the clock input. One input channel of the digitizer 610 accepts the pulse-echo trace from the ultrasound transmitter 150 and the other input channel accepts the $V^{AE}$ trace. Current levels can be monitored with a multimeter. Once the outputs from the digitizer 610 are complete, the data can be transmitted to a computer 190 for processing using acoustoelectric software packages described above and displayed on a display as co-registered images, i.e. an anatomy image obtained from pulse-echo shown in FIG. 3 as B-mode ultrasound image against the current source density image (USCDI).

Method of Mapping a Current Source

FIGS. 5 & 6 show some embodiments of how to use the current mapping and imaging system described above to map and image current densities and fields in living tissue in accordance with the present disclosure in greater detail. A generalized scheme for carrying out the present method is provide in block format in FIG. 5. Various additions can be made to an embodiment described in FIG. 5, for example the addition of blocks 500-550. In some embodiments, the current mapping and imaging systems described herein can be used to accurately and sensitively map current source densities or current fields present in electrically active tissue. Conventional reconstruction algorithms using multiple surface or depth electrodes are problematic due to conventional reconstruction algorithms using multiple surface or depth electrodes. Such a method is problematic due to the spread of electric field lines from each source and variations in the dielectric properties of different types of tissue. The inverse solutions in these cases are often ill defined and usually require assumptions about the underlying current source (e.g., monopole or dipole). Even in the best case with a large number of recording electrodes (e.g., 64 grid electrodes), these solutions provide merely a probability of the location of the source in 3-D space.

In some embodiments, current source densities can be measured, mapped and imaged by placing two or more recording electrodes connected to an electrically active living tissue to be mapped. In some embodiments, the living tissue in block 300 can include any known electrically active tissue, for example muscle, cardiac tissue, neural tissue, nerves, neurons, electrically active cells, components of cells, including cell membranes, artificial membranes and the like. The electrodes in block 300 can be placed in a conductive path traveling through the living tissue or in the vicinity of the living tissue. In general, the closer the recording electrodes are to the current source the more accurate the reconstruction of its location using the systems described in the present disclosure. For example, in some embodiments, the electrodes can be implanted into tissue to determine current sources that are internal to the tissue surface. In some embodiments, in particular for neural or brain current density imaging, the recording electrodes can be used that are part of preexisting neural recording devices and interventional neurosurgical devices presently used to determine electrical activity in the brain. In stiff further embodiments, the electrodes can be spaced apart and record voltages that are in the path of the electrodes to make the recording truly non-invasive.

Once the electrodes are fixed, the ultrasound transducer of block 310 is placed in acoustic contact with the body or living tissue to be sampled. As used herein acoustic contact can include the capability of focusing a beam of ultrasound into a desired location in a living tissue to be mapped. In some embodiments, the ultrasound transducer can be placed in proximate contact with the patient and directed to focus a beam with a focal length that is sufficient to provide a focal zone in a location within the current field or current source. In some embodiments, the living tissue is scanned over one or more trajectories to map an area of tissue to identify an electrical aberration such as an epileptic foci, a re-entrant cardiac pathway among others. In these applications, the ultrasound transducer can be placed on a catheter or other electrical mapping tool and inserted into the body in the vicinity of the living tissue to be sampled and moved in an XY, XZ or YZ vector plane within the body. In some embodiments, the ultrasound transducer can be mounted onto a mechanical or electronic stage and positioned in different locations in acoustic contact with the living tissue to be mapped to obtain a 2-D or 3-D current density map. The distance between the transducer element or elements and the current source or current field can be varied according to the focal length variation of the transducer, the density of the living tissue comprising the current source or current field and the size of the focal zone required for mapping the current source.

Once the recording electrodes of block 300 and the ultrasound transducer are in position, the ultrasound transducer can be connected to an ultrasound transmitter that times the sending of each pulse of ultrasonic wave towards the living tissue to map the current source. Once all of the "front end" devices are connected (the ultrasound transducer, transmitter and recording electrodes) the clinician can perform block 330.

Block 330 enables the clinician to start mapping process by directing the ultrasound beam to a location either in between the recording electrodes, in the vicinity of the recording electrodes or sufficiently close to the recording electrodes to enable the detection of voltage modulation due to the interaction between the ultrasonic pressure wave and a current source or current field. Block 30 can be carried out manually by a clinician or the step can be carried out automatically using a mechanical navigation device or a mechanical or electronic steering stage operably connected to the ultrasound transducer. In some embodiments, the area within a mapping field to be scanned can be a as small as a few cells in diameter to as large as multiple centimeters. Once the transducer has been placed into position via block 330, the firing of the beam occurs in block 340 in which a pulse is sent from the ultrasound transmitter to the ultrasound transducer to emit an acoustic wave. In some embodiments, the pulse is determined by the negative and positive waveform of the current propagating through the current field or mapping field. Once the acoustic wave has been fired, it travels along the beam of the transducer as shown in block 350.

The acoustic wave transmitted in block 350 can in some embodiments produce at least two different effects. As shown in block 360, the acoustic wave forms a focal zone, such that is there is a current source within the focal zone, a voltage modulation occurs, such that the phase and magnitude of the resultant AE signal ($V^{AE}$) depends on both the ultrasound pressure and applied current. Hence the magnitude of the $V^{AE}$ signal is proportional to the electric current at the current source and can be mapped and imaged in relation to the current density of surrounding pulsed locations. The $V^{AE}$ signal can be measured using a plurality of recording electrodes positioned in block 300. In some embodiments the measuring block 370-410 can consist of the steps: a. separating the high frequency acoustoelectric voltage signal from the low frequency voltage signal by filtering said voltage signal with an analog signal conditioner; b. amplifying the acoustoelectric voltage signal; c. sampling the amplified acoustoelectric voltage signal; d. digitizing the sampled acoustoelectric voltage signal; and e. storing the digitized acoustoelectric voltage signal in memory. In some embodiments, once the voltage signal is captured by the recording electrodes, the voltage signal can be filtered and amplified in accordance with blocks 380 and 390.

Once the $V^{AE}$ signal is separated from the $V^{LF}$ signal, the $V^{AE}$ signal can then be sampled and digitized in accordance with block 400. The resulting digitized signal can then be digitized and stored in memory. Once block 410 has been completed the mapping method disclosed in the present disclosure interrogates whether the 2-D or 3-D frame is complete as shown in block 420. As used herein, a frame can be a collection of beams. If no then the method proceeds to block 425 which issues a direction to aim the ultrasound transducer to another location by aiming the ultrasound beam as in block 340 in another direction. If the 2-D or 3-D frame is complete, a new interrogation is made as shown in block 430. If another frame is required, the method provides that the ultrasound transducer is aimed to a new location by performing block 330.

If the method does not require any additional frames to be collected, the data representing the $V^{AE}$ acoustic signal and optionally ultrasound image data taken with the same beam pulsed in block 330, is retrieved from memory. In some embodiments, the $V^{AE}$ signal data can be co-registered with other position data corresponding to the location of the focal zone of the pulsed ultrasonic wave in block 360 within a mapping field. Further examples of co-registerable data indicating the position of the current source can include MRI image data, CT scanning data, X-ray/fluoroscopy data (taken in real-time or preoperatively), optical imaging data of the tissue being mapped (also in real-time or preoperatively). In some embodiments, the $V^{AE}$ signal can be co-registered with a pulse-echo image obtained concurrently with the $V^{AE}$ signal and displayed concurrently for image guidance and current mapping.

The data comprising the $V^{AE}$ signal and optionally the co-registerable image data can be digitally filtered as shown in block 450. Once the data is filtered, the current sources or current density can be imaged on a display in 2-D or in 3-D optionally overlayed with position data of the current source obtained by any mapping process, including for example, pulse-echo ultrasound images, MRI image data, CT scanning data, X-ray/fluoroscopy data (taken in real-time or preoperatively) or optical imaging data of the current source within at least a portion of the mapping field being produced by the imaging system.

In some embodiments, the processing step used to convert the $V^{AE}$ signal to a positional coordinate and magnitude of the current source can include the steps of reconstructing the position of the received acoustoelectric voltage signal from two or more recording electrodes by applying a reconstruction algorithm (described below) to the digitally conditioned acoustoelectric voltage signal.

In some embodiments of the present disclosure, a method of mapping and imaging a current source in an electrically active living tissue can include the steps of: placing a plurality of recording electrodes within a mapping field and substantially near or in contact with a living tissue having a current field. At least one of the plurality of recording electrodes can be disposed within the mapping field to detect a voltage signal. The voltage signal can comprise two voltage waveforms, the first a high frequency acoustoelectric voltage signal and the second a low frequency voltage signal. Next the ultrasound beam can be directed to at least one position in the current field to record the $V^{AE}$ at that current source if present. The ultrasound transducer transmits an ultrasound wave to the at least one position in the mapping field. If a current source lies within the focal zone of the ultrasound beam, the recording electrodes can measure a voltage signal at the position comprising a high frequency acousticelectric voltage signal and a low frequency voltage signal produced at a position located at an intersection between a focal zone of the ultrasound beam and said current source through the plurality of recording electrodes. The computer, signal conditioners and digitizers processes the received acoustoelectric voltage signal to derive position data of said current source, the data comprising data points, each data point consisting essentially of a magnitude of said current source sampled at said position relative to said mapping field in said living tissue. The data points are stored in memory for later processing and/or retrieval by the computer. The computer converts the data points stored in the memory to an image representing a density of current within at least a portion of the mapping field; and displays the image on a display.

IN some embodiments, methods for mapping and imaging a current source density can include the steps of A method for mapping a current source density in an electrically active living tissue, the method comprising: providing a current source mapping device including an ultrasound emitting device operable to produce an ultrasound wave directed to a current source. a voltage recording device operable to record said acoustoelectric voltage signal produced by said current source, a voltage processing device operatively connected to said voltage recording device and a display. The ultrasound wave produces or induces an accoustoelectric voltage signal at the current source, The next step can include directing one or more ultrasound waves to a position in a mapping field containing the current source so that upon contact of the current source with the ultrasound wave, an acousticelectric voltage is produced in proportion to a current density of the current source in the mapping field, within the living tissue and the voltage processing device can process the acoustoelectric voltage signal into a digitized representation of the current density at the current source and displaying the digitized representation of the current density on the display.

The methods of the present disclosure can be modified in accordance with the particular current source mapping application undertaken. For example, as shown in FIG. 6, in one embodiment a method for neural recording and electrical current mapping (Ultrasound current source density imaging) will be provided in detail. Because each brain has a complex and unique spatial organization, the neurosurgeon uses functional brain mapping to locate areas vital for especially movement, sensation and language. Pre-surgical diagnostic imaging tools, like scalp electroencephalgy (EEG) and functional magnetic resonance imaging (fMRI), provide only a loose representation of the location of these critical areas with a spatial resolution on the order of 1 cm or greater. These maps also change over time due to, for example, learning or injury induced cortical plasticity. Consequently, the neurosurgeon relies heavily on real-time pinpoint electrical mapping of the brain during surgery in the region close to the epileptic focus. Such mapping improves the chances of a successful surgery with the ultimate goal being complete removal of the abnormal brain tissue, while retaining eloquent brain areas critical for everyday life.

Electrical brain mapping for treatment of epilepsy begins with the cerebral cortex exposed and the patient alert and responsive to various sensory, motor and electrical stimuli. The laborious procedure, which generally lasts several hours, is central for pinpointing functional brain areas and guiding the neurosurgeon in determining the boundaries for resection. FIG. 6 depicts a seizure captured on a preoperative fMRI (left and bottom) along side an illustration of the surface of brain captured during neurosurgery. The brain can be physically labeled according to its corresponding function (not shown). All too often the neurosurgeon is confronted with a narrow window of success: failure to remove enough symptomatic tissue could lead to recurrence of epileptic seizures, whereas resection of too much eloquent cortex could cause permanent neurological deficits, from slurred speech to partial paralysis. Pre-surgical diagnostic images (e.g. MRI) and real-time ultrasound-aided 3-D navigation systems are registered with the location of the electrical recording and stimulation sites. This imaging technology facilitates the mapping procedure, which has two principal objectives during treatment of epilepsy: 1) locate eloquent brain areas critical for survival and 2) identify and map an epileptic seizure as it evolves during the surgery. Bipolar stimulating electrodes activate a specific brain region while the patient reacts to an assortment of cognitive tasks and stimuli.

As shown in FIG. 6 a clinician places multiple electrodes (grid of 64, GND Electrode) placed on the surface of the cortex that simultaneously record from several brain areas (Ad-Tech Medical, Inc., Racine, Wis. USA). These electrodes are used to monitor electrical activity and map an epileptic seizure during the surgery. Based on the results of electrical mapping, the neurosurgeon determines the eloquent cortical areas, topology of the epileptic focus and optimal boundaries for resection based on the acoustoelectric (AE) effect, to image electrical current flow using moderate ultrasound pressure combined with surface recording electrodes. Imaging biopotentials obtained using the systems and methods of the present disclosure improves spatial contrast and resolution of traditional electrophysiology by constraining the detected signal to where the ultrasound and current wave fields intersect. An integrated imaging system based on the methods disclosed in the present disclosure has several potential advantages over current methods, such as superior spatial resolution and three dimensional imaging of current vector fields, with as few as two recording electrodes on the surface of the brain. Moreover, the present current source density imaging system and methods could potentially be controlled by electronic steering of the ultrasound beam and integrated into existing ultrasound imaging equipment normally used during navigational neurosurgery. Such a combined system could provide simultaneous ultrasound, Doppler blood flow and electrical current flow imaging, which would greatly facilitate electrical brain mapping during interventional neurosurgery for treatment of epilepsy.

With reference to FIGS. 7A and 7B, the 2-D mapping of current source present in a nerve phantom and a living lobster nerve cord are shown. FIGS. 7A and 7B correspond to the experimental results obtained from the mapping system setup described in FIGS. 1A and 1B respectively. A cross sectional scan of a nerve phantom produced the 2-D images portrayed in FIG. 3 of the pulse echo (first row) and AE signal (second row). A 500 kHz transducer (f/# 1.1, f=100 mm) was translated over 10 mm (1 mm step size) to produce the images. Both magnitude (column) and wavefield plots (column 2) are consistent with the simulation results exhibited in row 3, especially in terms of resolution along the ultrasound propagation axis. The measured image has slightly lower lateral resolution, which is matched by the pulse echo signal, possibly due to the annular shape of the transducer, which was not accounted for in the simulation. A peak current density of 100 mA/cm$^2$ and focal pressure of 2 MPa were used to generate the AE signal. Dynamic ranges were 20 dB and 10 dB, respectively, for pulse echo and AE images. When the current level was reduced close to the physiologic range (10 mA/cm$^2$), the peak signal was still 6 dB above the noise level. All images were interpolated to 100 µm in both lateral and axial directions. The down shifted frequency spectrum of the recorded AE signal (0.3 MHz compared to the pulse echo center frequency of 0.5 MHz) was consistent with the simulation and reflects the distribution of pressure and current gradient fields. These pressures are considered moderate and within the range of clinical ultrasound imaging intensities.

As shown in FIG. 7B, cross sectional images of an abdominal nerve cord using a 7.5 MHz ultrasound transducer (f/#=5, f=50.8 mm) are illustrated. The pulse echo image (PE) indicates that the diameter of the section is less than 2 mm, which is consistent with the AE image in the direction of the ultrasound beam axis. The increased lateral resolution can be due to the relatively large f/# and lateral beam size of the transducer element. This is confirmed with an AE simulation with a cylinder diameter of 1.4 mm. The effective current field is likely smaller than the actual diameter of the nerve cord based on the thick sheath with high axial resistance surrounding the lobster nerve cord. A simulation (AE Simulated) with an effective diameter of 0.8 mm approaches the experimental result. A current density of 80 mA/cm$^2$ was used to generate the measured AE signal with a scan resolution of 0.3 mm. Dynamic ranges for the plots were 40 dB for the pulse echo and 20 dB for the AE images.

Cardiac Waveform Propagation and Mapping Using Ultrasound Current Source Density Imaging In some embodiments, cardiac mapping of current fields can be performed using a method in accordance with the present disclosure. Conventional methods for mapping cardiac current fields lack either spatial resolution (e.g. ECG) or are time consuming (e.g., intra-cardiac catheter electrode mapping). We present a method based on the acoustoelectric effect (AEE) with potential for rapid mapping of current fields in the brain, heart or any electrically active tissue with high spatial resolution. The AEE is a pressure-induced conductivity modulation, in which focused ultrasound can be used as a spatially localized pressure source. When an ultrasound beam is focused between a pair of recording electrodes in a homogeneous conductive medium, an induced voltage will be produced due to the pressure-modulated conductivity and local current density. The amplitude of the voltage change should be proportional to fluctuations in current density, such as those for example generated during the cardiac cycle, impulse conduction or muscle polarization, in the region of focused ultrasound. In some embodiments a 540 kHz ultrasound transducer is focused between two tin electrodes lying parallel to the beam axis. These electrodes inject current into a 0.9% saline solution. A pair of insulated stainless steel electrodes exposed at the tip is used to record voltage. In some embodiments, to simulate a cardiac current, a low frequency current waveform is injected into the sample such that the peak current density (8 mA/cm2) approximates cardiac currents. The transducer is pulsed at different delays after waveform initiation. Delays are chosen such that the low frequency waveform is adequately sampled. Using this approach an emulated ECG waveform can be successfully reconstructed from the ultrasound modulated voltage traces.

As shown in FIG. 8A, an $V^{AE}$ wavefield is shown illustrating the difference between the waveform recorded at 8 mA/cm$^2$ and the waveform recorded at 0 mA/cm$^2$ FIG. 8B shows a current waveform which simulates a propagating cardiac sinus rhythm. FIG. 8C illustrates the results of the present current source density mapping method by overlaying a simulated sinus cardiac current propagation over the experimentally acquired AE signal based current source density map using the methods and systems of the present disclosure.

Improving the Signal to Noise Ratio of the AE Signal

The present ultrasound current source density imaging and mapping system and methods provides for a linear relationship between the AE signal and current and pressure presently used for ultrasound imaging (i.e. <2 MPa). The linear relationship observed in practice with living tissue current source density mapping between the AE signal and current and pressure is consistent with Equation 2.

The present current source density mapping system and methods described herein further include methods for improving the sensitivity of the system for low current density detection and mapping. All of these experimental variables can be manipulated by a physician and/or electrophysiologist/radiologist to best improve spatial resolution and improve the signal to noise ratio required for detecting and mapping the current sources of these divergent tissues. For example, the present disclosure provides for methods and systems for increasing the signal to noise ratio (SNR) to detect and map all biological current sources and biopotentials in living tissue.

Pulse sequencing and coding algorithms may play an important role in maximizing the SNR without exceeding the maximum exposure level. Examples of coded waveforms in ultrasonic imaging contemplated herein can include components, such as chirps added to the basic system components, to enhance sensitivity and spatial resolution in ultrasound imaging. There are three main advantages to using coded pulse waveforms 1) increase penetration; 2) increase SNR; and 3) increase frame rate. Electrical brain mapping with the current mapping systems and methods of the present disclosure could especially benefit from the latter two. An increased frame rate would allow for additional temporal averaging. Waveforms that extend the time-bandwidth product of the ultrasound beam without sacrificing spatial resolution can improve the SNR by more than 15 dB. The following equation has been used to estimate improvement in SNR for diagnostic ultrasound imaging:

$$^{Tp}SNR_i = \frac{\int p_i(t, \vec{r_i})dt}{P_{Noise}} \quad (2a)$$

with pressure pi at axial position r, total duration of received echoes Tp, and band-pass thermal noise P noise. Frequency modulated coded excitation can be been incorporated into some clinical scanners to improve the SNR in diagnostic ultrasound without sacrificing spatial resolution. A correlation filter on a pulse-compression waveform readjusts the phases and preserves the high spatial resolution of a short pulse. In some embodiments of the present disclosure, the amplitude of the AE signal and sensitivity of the current density mapping system can be optimized by comparing coding schemes sent through a power amplifier (ENI Inc). Recording electrode properties can also affect the sensitivity of the current source density mapping system described herein. Specifically, the impedance, geometry and distance (r') to the voltage source (Ve) all affect the lead field Jm of the recording system.

Without wishing to be bound by theory, a monopole in an infinite homogenous medium of conductivity σ, the potential decays by a factor of 1/r'. The 1/r factor is also a good approximation for heterogeneous soft tissue. The sensitivity of the recording electrodes can also be affected by background noise. Although thermal noise scales according to √Hz the primary sources of noise for in vivo electrophysiology experiments are related to breathing, cardiac activity (ECG) and 60-Hz line noise. Each of these low frequency sources can adversely affect conventional electrical brain mapping. With the system and methods to map the current source density in a living tissue of the present disclosure, however, the detected AE signal is in the MHz band, far away from typical physiologic noise sources. Primary sources of MHz noise in the hospital come from MRI scanners and radio towers that transmit at MHz frequencies. Each of these noise sources can be reduced by metallic shielding. If these noise sources affect the sensitivity of the present current source density mapping system, a Faraday cage can be implemented to isolate environmental noise sources. Other random noise sources (e.g., thermal) can be reduced by trial averaging. In some embodiments, methods to reduce the existence of noise can include: implementing electrode impedances ranging from 100Ω to 1 MΩ, and adjusting the distance between the electrode and induced voltage source (i.e., at the ultrasound focus) to further optimize the sensitivity of the present mapping system.

The total SNR of the AE signal with a plurality of recording electrodes can be evaluated at different pulse pressures and current densities. Although grid electrodes implemented during interventional neurosurgery cover a large portion of the exposed brain, depth electrodes are occasionally used to penetrate under the surface of the cortex; in such circumstances, sensitivity of the present current source density methods and systems described herein may be further improved by moving the electrode closer to the voltage or current sources. Nonetheless, one major advantage of current source density mapping according to the present disclosure, is the generation of 2-D or 3-D images of current flow without the need for invasive depth electrodes. Finally, although as few as two electrodes can be used to generate 3-D images of current flow, a multielectrode system could still provide higher sensitivity by enabling multi-point averaging and coincident detection. With experiments and simulation, the methods provided herein provide for interfacing electrode arrays with a neural chamber and evaluate the SNR. The present current source density mapping system described herein can utilize different types of recording electrode arrays in acute and chronic preparations (e.g., Michigan probes and grid electrodes commercially available from Ad-Tech (Racine, Wis. USA).

A. Theoretical Considerations in Calculating and Processing the $V^{AE}$ Signal Lead Fields and Voltage Measurement The sensitivity distribution of a pair of electrodes is called a lead field, which is represented as a vector field with dimensions of m$^{-2}$. Its shape and distribution are the same as that of the electric field when unit current is injected through the electrodes. By convention, the sign of the lead field is opposite to the electric field. The voltage measured by lead i, $V_i$, due to a distributed current source $J^I = J^I(x,y,z)$ is $$V_i = \iiint \rho(\vec{J_i^L} \cdot \vec{J^I})dxdydz, \quad (3)$$

where $\tilde{J}_i^L = \tilde{J}_i^L(x,y,z)$ is the lead field of lead i and $\rho=\rho(x,y,z)$ is the resistivity. Integration variables (such as x, y and z) are omitted from subsequent equations, except when needed for clarity.

B. The Acousto-Electric Signal Equation

An approximation of the AE signal equation, relates to the resistivity change seen by an arbitrary electrode recording system due to a spatially distributed pressure field. In some embodiments of the present disclosure, methods are provided for deriving the AE signal equation for focused ultrasound using a more complex model of the pressure field as illustrated in FIG. 9A. At time t the ultrasound pressure field is $\Delta P = \Delta P(x,y,z,t)$ and using equation (1) the resistivity distribution is $$\rho = \rho_0 - K_I \rho_0 \Delta P. \tag{4}$$

Substituting (4) into (3) leads to $$V_i = \iiint (\tilde{J}_i^L \cdot J^I)(\rho_0 - K_I \rho_0 \Delta P) dx\, dy\, dz. \tag{5}$$

Expanding $V_i$ gives $$V_i = \underbrace{\iiint (\tilde{J}_i^L \cdot J^I)\rho_0 dx\, dy\, dz}_{V_i^{LP}} + \underbrace{\iiint (\tilde{J}_i^L \cdot J^I)(-K_I \rho_0 \Delta P) dx\, dy\, dz}_{V_i^{AE}}. \tag{6}$$

The first term, $V_i^{LF}$ represents the low frequency (DC—10 kHz) content of $V_i$ while the second term $V_i^{AE}$ represents the high frequency (MHz) AE signal. In practice $V_i^{LF}$ and $V_i^{AE}$ can be separated using analog and digital filters. Within $V_i^{AE}$ we expand the ultrasound pressure factor, $\Delta P$, into its subcomponents such that $$\Delta P(x,y,z,t) = P_0 b(x,y,z) a(t-z/c), \tag{7}$$

with ultrasound beam pattern $b(x,y,z)$ defined with respect to the transducer at the origin (the origin is at the center of the circular bath), $P_0$ the amplitude of the pressure pulse, and $a(t)$ the pulse waveform. Inserting equation (7) into equation (6) we rewrite $V_i^{AE}$ as $$V_i^{AE}(x_1, y_1, t) = -K_I \iiint (\tilde{J}_i^L \cdot J^I)\rho_0 b(x-x_1, y-y_1, z) P_0 a\left(t - \frac{z}{c}\right) dx\, dy\, dz, \tag{8}$$

where $V_i^{AE}(x_1, y_1, t)$ represents the voltage trace measured by an electrode recording system that has a lead field $\tilde{J}_i^L$ with the ultrasound beam translated to $(x_1, y_1)$, $J^I$ the current distribution and c the speed of sound.

C. The Sifting Property of the Ultrasound Beam in Current Source Density Mapping Traditional inverse methods reconstruct electric current density from voltage measurements using equation (3). This is a projection of the entire unknown current density field onto the lead field of the recording electrode. To resolve the current density distribution on an N×M grid, with N and M integers, at least 2NM independent measurements are required; otherwise the problem is underdetermined.

The AE signal equation is essentially the same as equation (3) except for the multiplicative factor of the ultrasonic beam pattern. The focal volume of a beam $b(x,y,z)$ is typically an ellipsoid with short axis diameter of 1 mm and long axis diameter of 3-4 mm. By contrast, the integration volume of a lead is on the order of centimeters. Because $b(x,y,z)$ is small compared to the integration volume, it acts as a sifting function similar to a Dirac delta function. The AE voltage measurement is, therefore, only proportional to the projection of $J^I$ onto the lead field local to the focal zone, not the entire field. Furthermore, the MHz frequency of $a(t)$ is a spatial label distinguishing it from the low frequency voltage, $V_i^{LF}$, also simultaneously measured by the electrodes.

The sifting property of $b(x,y,z)$ is illustrated in FIG. 9A where the beam spot is presented as a dashed circle. Two different recording leads 1 and 2 are shown, which correspond to two different positions of the mobile recording electrode M. Since $\tilde{J}_1^L$ is anti-parallel to $J^I$ within the beam spot, the AE signal measured by lead 1 is relatively large. By contrast, as $\tilde{J}_2^L$ is roughly orthogonal to $J^I$, we expect the AE signal measured by lead 2 to be small. From this example, clearly $J^I$ cannot be obtained using only one lead. To solve $J^I$ from AE measurements, current source density mapping requires at least one independent lead field for each spatial dimension. That is, two measurements are required for a 2-D geometry, and three for a 3-D geometry. This is, however, a great improvement over conventional methods since only 3 leads are required to yield a fully determined inverse problem, and still retain good spatial resolution. The sifting property of $b(x,y,z)$, as well as the spatial label of the high frequency of $a(t)$, are two key enhancements to electrical mapping with methods and systems described in the present disclosure.

D. Acousto-Electric Signal Measurement and Processing

As illustrated in FIG. 9B an experimental setup designed to generate and detect the 2-D current distribution or orientation of the current sources in a mapping field. In some embodiments, a low frequency sinusoidal current (arbitrarily chosen to be 500 Hz in FIG. 9B) with peak amplitude of either 28 mA or 0 mA (control) can be injected through a pair of AgCl electrode wires (0.15 mm diameter), marked "+" and "−" into a 1-mm bath of 0.9% NaCl placed in a circular container (38.1 mm diameter). At low frequencies (<1 kHz), saline and tissue are primarily resistive, and the alternating current reduces polarization at the electrode interface compared to direct current. Also, at 500 Hz, the frequency of the injected current is much lower than the ultrasonic frequency of the AE signal, which can be easily filtered from the detected voltage. Stimulating AgCl electrodes were used for their electrochemical stability. The bottom of the container was a thin plastic film acting as an acoustic window. A 5-mm thick layer of mineral oil was placed on top of the saline to insulate to conductive saline layer, The mineral oil allowed the acoustic wave to pass through the saline window and minimized surface reflections at the saline interface.

Ultrasound can be operably coupled to this container with de-ionized water (DI-$H_2O$). The current waveform generated by a signal generator (33120A, Agilent, Santa Clara, Calif.), amplified (MDT694, Thorlabs, Newton, N.J.) and can be AC coupled to the electrodes. The current can be monitored using a multimeter (Toolkit 2707A, BK Precision, Yorba Linda, Calif.), as well as a differential amplifier, which measures the voltage across a 1-ohm resistor placed in series with the current injecting electrodes. An AgCl electrode fixed at 0° can be used as the recording reference, while a mobile tungsten electrode can be rotated around the boundary to record voltages in 2-D in 20° steps from −60° to 260° (N=17). A 7.5 MHz single element ultrasound transducer with a diameter of 1.27 cm and focal length of 5.08 cm can be used to focus the membrane from below. In some embodiments, an ultrasound transducer can be raster scanned in the xy-plane covering a 16×17 pixel grid with a step size of 2.2 mm in each direction. The current generator (33120A, Agilent) can be provided as the master trigger for the experiment at the start of each cycle. The current can be fed into a Field-Programmable Gate Array (FPGA) (ezFPGA, Dallas Logic, Plano, Tex.), which can issue a trigger to an ultrasonic pulser/receiver (5077PR, Panametrics Inc., Waltham, Mass.) and a digital acquisition board (DAQ) (PDA12, Signatec, Newport Beach, Calif.) at either the maximum or minimum or both of the current waveform. At each location, the transducer can be pulsed from 1 to 512 times, or 128 times on both the maximum and minimum of the current waveform. The AE signals corresponding to the positive peak can be averaged, as well as those corresponding to the negative peak. The average AE signal from the positive current peak is subtracted from the AE signal of the negative peak to remove common-mode noise, such as transducer ringing.

To measure the AE signal, each electrode can be connected via an analog high pass filter (480 kHz cut off frequency) to a differential amplifier (1855A, LeCroy, Chestnut Ridge, N.Y.) with a predetermined gain of about 1 to about 150 dB. In some embodiments, the predetermined gain can be 10-100 db. The amplifier can also have a bandwidth of 20 MHz. The output from the amplifier can optionally be further amplified by an additional 29 dB (5072PR, Panametrics Inc.). In some embodiments, the AE signal and pulse echo can be optionally sampled concurrently at 50 MHz and digitized with 12-bit precision. The resulting data can be processed in Matlab™ (MathWorks Inc, Natick, Mass.). Signals can be bandpass filtered between 1 and 3 MHz and converted to analytical form in Matlab™. Since the phantom in FIG. 9A was a saline bath bounded on one side by a plastic membrane and mineral oil on the other, the conductivity profile along the beam axis is approximately rectangular. If the membrane is not perfectly flat, the timing of the pulse echo of the membrane can be used to shift the AE signals to align them to the same time index. Based on the correlation scheme described below, the signals are assumed identical in shape and differ only in magnitude and sign.

To assign values to the 2-D grid, a representative AE template waveform [one with good signal to noise ratio (SNR)] can be chosen and correlated with all other AE waveforms. Under the assumption that the AE signals are aligned, the value at zero lag in the cross correlation sequence was chosen as the representative measured value at each grid point. Correlation detection was used to filter out noise spikes within the bandwidth of the AE signal. In some embodiments, such a process yields 17 images arranged in a 16×17 pixel grid, one image per angle of the recording electrode. Each AE image is the result of the dot product of the unknown current field and the lead field of the recording electrodes. The next section explains decoupling of recording electrodes from the measured AE signal.

E. Conventional Low Frequency Mapping of the Field

The dipole current field was independently measured using conventional methods to compare results of current source density mapping reconstruction and simulation in accordance with the present disclosure. The potential distribution in the mapping field can be mapped with a mobile tungsten electrode, mounted on a motorized 2-D translation stage and scanned across a 25×24 step grid in steps of $\Delta x=\Delta y=1.5$ mm. The potential can be measured with respect to a fixed reference placed on the boundary of a mapping field or circle at angle 0° using a differential amplifier (1855A LeCroy). The geometry is illustrated in FIG. 9B to the right. The output of the amplifier can be sampled and digitized using an oscilloscope (TDS1002, Tektronix, Beaverton, Oreg.) and transferred to a computer for storage. The magnitude and sign of the trace corresponding to each pixel can be measured. In addition, boundary voltages can be measured using the same instrumentation and signal processing except that the recording electrode can be rotated around the boundary of the saline bath in 32 steps of 10° from −60° to 250°.

F. Current Source Reconstruction: the Forward Problem of a Single Dipole

The forward problem relevant to the current source density mapping methods of the present disclosure is finding the measured boundary voltage distribution produced by a point dipole current source. Rewriting equation (3) in two dimensions yields $$V_i = \iint \rho (\tilde{J}_i^L \cdot J^I) dx dy, \tag{9}$$

with $J^I = J^I(x,y)$, $\tilde{J}_i^L = \tilde{J}_i^L(x,y)$ and $\rho = \rho(x,y)$. A single point dipole source $J_0^I$ at location $(x_1, y_1)$ gives $$J^I(x,y) = J_0^I \delta_2(x-x_1, y-y_1), \tag{10}$$

with $\delta_2(x,y)$ the 2-D Dirac delta function, which produces the lead voltage $$V_i = \rho(x_1, y_1)(\tilde{J}_i^L(x_1, y_1) \cdot J_0^I). \tag{11}$$

If we have N leads, the vector of boundary voltages $$V = [V_1 V_2 \ldots V_N]^T \tag{12}$$

(where $[*]^T$ indicates transpose) is related to $J_0^I$ at $(x_1, y_1)$ by a N×2 transfer matrix T $$T(x_1, y_1) = [\tilde{J}_1^L(x_1, y_1) \tilde{J}_2^L(x_1, y_1) \ldots \tilde{J}_N^L(x_1, y_1)]^T \tag{13}$$

by $$V = \rho(x_1, y_1) T(x_1, y_1) J_0^I. \tag{14}$$

Equation (14) is the solution to the forward problem. That is, the relationship between the source $J_0^I$ and the boundary voltage is determined. Typical inverse algorithms solve the forward problem for all points (x,y) and calculate the normalized sum squared error (NSSE) between the measured and estimated boundary voltage distribution for each point. The normalization factor is the maximum error. The algorithm ranks the pixels in terms of likelihood (1—NSSE). The pixel likeliest to contain the dipole is the one that minimizes the sum of squares error between the measured and calculated boundary voltage distribution. We directly compare this algorithm with current source density mapping in accordance with the present disclosure.

G. Current Source Density Reconstruction Algorithm

To derive the current source density reconstruction algorithm in some embodiments described herein, the signal equation (8) is rewritten and simplified. In the special case of an infinite saline film of thickness h and uniform resistivity $\rho'$, the 3-D resistivity distribution is $$\rho(z) = \rho'(u(z) - u(z-h)), \tag{15}$$

where u(z) is the step function. We further assume that the thickness h is small enough such that the recording lead field $\tilde{J}^L$ and unknown current field $J^I$ are primarily 2-D and the beam pattern b(x,y,z) has a constant cross section across the thickness of the bath $$b(x,y,z) = b(x,y), \quad 0 \leq z \leq h. \tag{16}$$

With the ultrasound focus at $(x_1, y_1)$, the voltage measured between the fixed reference and the mobile electrode at angle $\theta_i = i \Delta\theta$, $i=1, \ldots, N$ is $$V_i^{AE}(x_1, y_1, t) = -K_I P_0 \rho' \tag{17}$$

-continued $$\underbrace{\int\int (\tilde{J}_i^L(x,y) \cdot J^I(x,y))b(x-x_1, y-y_1)dxdy}_{A} \underbrace{\int_0^h a\left(t-\frac{z}{c}\right)dz}_{B}.$$

Based on these assumptions, A and B in (17) are convolutions. In convolution A, b(x,y) sifts out the value of the dot product at $(x_1,y_1)$, whereas B describes the generation of the high frequency component of the signal as the acoustic pulse transverses the saline bath.

For the development of the algorithm, we assume the beam is narrow, that is, $$b(x,y) \approx b_0 \delta_2(x,y). \quad (18)$$

By defining $$A(t) = \int_0^h a\left(t-\frac{z}{c}\right)dz \text{ and } K_a = -K_I P_0 \rho' b_0, \quad (19)$$

equation (17) becomes $$V_i^{AE}(x_1,y_1,t) \approx K_a(\tilde{J}_i^L(x_1,y_1) \cdot J^I(x_1,y_1))A(t). \quad (20)$$

From equation (20), it is clear that the exact time point of A(t) does not affect the reconstruction, so for the sake of argument we choose here the maximum, $A_0 = \max\{A(t)\}$.

$$V_i^{AE}(x_1,y_1) \approx K_a A_0(\tilde{J}_i^L(x_1,y_1) \cdot J^I(x_1,y_1)). \quad (21)$$

Now equation (21) has the same form as (11) except that the boundary voltage $V_i^{AE}$ is also a function of space. Dropping the superscript on $V_i^{AE}$, equation (14) becomes $$V(x_1,y_1) \approx K_a A_0 T(x_1,y_1) J^I(x_1,y_1) \quad (22)$$

The minimum normalized estimate of the dipole, $J^I(x_1,y_1)$, given $V(x_1,y_1)$ is $$J^I(x_1,y_1) = \frac{1}{K_a A_0}(T(x_1,y_1))^+ V(x_1,y_1). \quad (23)$$

where $(*)^+$ denotes a Moore-Penrose pseudo inverse (i.e., $T^+ = (T^T T)^{-1} T^T$).

To determine the transfer coefficients, the lead fields $\tilde{J}_i^L(x_1,y_1)$ can be calculated for each angle on the same 16×17 pixel grid used in the experiment. The AE data can be simulated by calculating the lead fields and the current distribution $J^I(x,y)$ on a high density 241×257 grid with $\Delta x = \Delta y = 0.137$ mm and then calculating their dot product. From equation (16), the AE signal measures the dot product $\tilde{J}_i^L(x_1,y_1) \cdot J^I(x_1,y_1)$ with low pass filtering by the ultrasound beam. Therefore, to simulate the effect of the ultrasound beam pattern, a Gaussian filter with a 3-mm diameter at −3 dB was applied to the high density dot product data. The result was then downsampled to the same 16×17 pixel grid used in the experiment. For the low frequency simulation, this upsampling/downsampling was not used, and no filtering was applied. The potential distribution was simulated and sampled on a 25×24 grid with 1.5-mm step size. The low frequency boundary voltage was sampled at 100 intervals, along the boundary of the domain.

Both AE and low frequency voltage signal measurements agreed well with simulation. The 2-D current field was successfully reconstructed by the methods described herein for current source density mapping, with the current source and sink located to within 1 mm of their actual locations. Current injecting electrodes extending above the saline bath prevented the entire region to be mapped, as illustrated in FIG. 9B. Nonetheless, the correlation coefficient between measured data and the simulated distribution for the remaining pixels (88% of total) is within the range of 0.900-0.999. Measurement closely matched simulation with a correlation coefficient of 0.999. The position of the stimulating electrodes prevented measurements between $\Theta=260°$ and 300°. The conductivity profile along the beam axis was approximately rectangular. The polarity of the AE signal follows the sign of current injection. In some embodiments, the method requires the subtraction of the "−" trace from the "+" trace, eliminating common-mode noise. Note that the AE signal is shifted down in frequency to approximately 3 MHz from the incoming acoustic pulse. This is consistent with convolution B in equation (17) stating that the AE signal is a convolution between the acoustic pulse and an averaging (low pass) filter with a rectangular shaped impulse response.

Even for a single lead of two electrodes, the location of the source can be highly resolved. Of the 16 other similar images—one for each position of the mobile electrode can be determined. All images produced can be used to reconstruct the current density as described by equations (22) and (23). Results using a conventional inverse algorithm (i.e., the likelihood as a function of space) finds the most likely location of a single dipole given the boundary voltage distribution and fails to provide the spatial resolution and sensitivity when compared to the methods used in the present disclosure to map a current source density.

The divergence of the current density is related to the current source density by equation (23). Reconstructions can be quantified by locating the current sources and sinks based on the extrema of the divergence distribution of the simulated and measured data. Simulations of the AE signal in some embodiments agreed well with AE and low frequency measurements. The reconstructed current field based on current source density mapping in accordance with the methods and systems provided by the present disclosure can locate the current source and sink to within 1 mm of the actual locations. Note that in some embodiments, the full-width-half-maximum (FWHM) values of the present method of current source density mapping can be dominated by the lateral dimensions of the focal spot of the ultrasound transducer, which can range from 0.5 mm to 10 mm, based on its center frequency (7.5 MHz) and f number (f/#=4).

In some embodiments, the present disclosure provides for methods to map current source densities based on the AE effect with improved spatial resolution. In the present disclosure, the methods described herein to determine and map the current source densities can be used to accurately locate a 2-D current source to within 1 mm of its actual position, without making apriori assumptions related to the source, other than the resistivity distribution. The accuracy was within one sampling interval of the grid step size (2.2 mm), The spatial resolution of current source density mapping methods described herein, according to the AE signal equation (17) is dominated by the properties of the ultrasound transducer due to the sifting property of the ultrasound beam. When sampling or pacing is required with a current generator, the thin current injecting electrodes (diameter=0.2 mm) can be considered point sources. The average FWHM of 4-mm for both simulated and measured data can be consistent with the beam width of the transducer (3 mm) and the applied smoothing filter. The lateral resolution can be improved by choosing a transducer with a tighter focus than the f/4. The beam spot size of a narrow band transducer is roughly equal to the product of the wavelength and f/number, where f/number is the ratio of the transducer's focal length to its diameter.

In some embodiments, a tightly focused transducer with f/1 at the same frequency can have a focal diameter of approximately 0.75 mm. The chosen inverse method represents the best-case scenario for conventional algorithms. The dipole source geometry dovetails with the explicit single-dipole assumption, and the algorithm uses multiple measurements with high SNR. In contrast, the method described in the present disclosure can directly resolve the location of the dipole's source and sink with only the assumption of the resistivity distribution, which is a necessary assumption of most inverse algorithms. Furthermore, the entire 2-D current field can be illustrated as an image of the x and y-components of the field. Direct estimates of the current field would not normally be possible using conventional electrical mapping methods. Although the present disclosure provides for methods wherein the current source density mapping reconstructs both the magnitude and direction of the current from a synthetic array of 18 electrodes, as few as two electrodes can provide detailed information on the actual location of a current dipole. Conventional dipole localization would require a large number of electrodes to approach similar results.

In some embodiments, the SNR of a reconstructed image can still be sufficient to accurately estimate the current source and sinks to within 1 mm. Although 3-D reconstruction faces additional challenges, equation (8) can still be separated into two factors: one that depends only on x and y and the other on z. In a 3-D reconstruction, the dependence of the beam pattern b(x,y,z) on z needs to be considered. If the ultrasound transducer and electrode array are fixed in position with respect to each other, a known electrical source can be used to self-calibrate the current source density mapping system. When the present methods provided in the present disclosure are applied to intracardiac electrocardiography, it could potentially generate 3-D current maps of the cardiac activation wave with excellent spatial and temporal resolution. High frame rate current source density mapping is possible via electronic ultrasound beam steering. Although existing catheters that integrate electrodes with ultrasound are limited to 2-D imaging, technology exists to steer 60°×60° sectors in 3-D, which can be implemented to generate 3-D images of current flow co-registered with pulse-echo images illustrating structure. The relative motion of the catheter might not be a significant problem, since the heart is quasi-stationary during the spread of the activation wave. Motion-compensation algorithms could be used to reduce artifacts associated with heart motion.

The present methods and systems for current source density mapping has unique advantages over other current density mapping methods because there is no registration error between anatomical images and maps of electrical activity. This is superior to conventional inverse localization methods that must use pre-surgical CT or MRI images for anatomical mapping fused with an electroanatomical map for catheter guidance. MRI and CT provide pre-surgical, static images of the heart and typically provide no functional information. Registration error between the CT/MRI images and the electro-anatomical map has been reported to be in the range of 2-10 mm. In some embodiments, the present system can be tailored to combine one or more recording electrodes with one or more ultrasound catheters, and can be used for anatomical mapping and guidance. Such a device used in current source density mapping in accordance with the present disclosure can generate pulse-echo ultrasound images showing myocardial anatomy and kinematics and can be simultaneously integrated with electrical mapping. Such automatic real-time co-registration is currently not found in typical cardiac imaging and would dramatically facilitate guidance during corrective heart surgery. The current field can be independently measured using a roving monopolar electrode. Both measurements are similar to the theoretical distribution. This method can be immediately extended to 3 dimensions and it has potential for use in rapid mapping of current fields in the heart with high spatial resolution.

What is claimed is:

1. A current source density mapping system comprising:
   a. an ultrasound transducer operable to emit an ultrasound wave traveling along an ultrasound beam directed at a mapping field in a region of living tissue and operable to provide a pulse repetition rate exceeding 10 kHz;
   b. an ultrasound pulser operable to deliver a transmit pulse to said ultrasound transducer;
   c. a timing device operable to produce controlled excitation of said transmit pulse;
   d. a plurality of recording electrodes operable to be positioned in contact with said living tissue and operable to detect an acoustoelectric voltage signal generated at a bioelectric current source and within a focal zone of said ultrasound beam;
   e. an amplifier operatively connected to said recording electrodes and operable to amplify said acoustoelectric voltage signal at a predetermined gain; and
   f. an analyzing component comprising a digitizer, a sampling device, a signal processor and a display unit operatively connected to said amplifier, said analyzing component operable to determine the location of said bioelectric current source relative to said mapping field by analyzing said acoustoelectric voltage signal detected by said recording electrodes in response to an interaction between said ultrasound wave and the presence of said bioelectric current source in said mapping field.

2. The current source density imaging system of claim 1, wherein the ultrasound transducer has a center frequency ranging from about 100 kHz to about 300 MHz and operable to produce a focal length ranging from about 1 mm to about 200 mm.

3. The current source density imaging system of claim 1, further comprising a current generator to produce AC current to said living tissues.

4. The current source density imaging system of claim 3, wherein said current generator comprises a plurality of electrodes in electrical communication with said current generator.

5. The current source density imaging system of claim 1, wherein said plurality of recording electrodes is selected from the group consisting of grid electrodes, depth electrodes, electrode arrays and combinations thereof.

6. The current source density imaging system of claim 1, further comprising a positioning system, wherein said positioning system controls the placement of said ultrasound beam in said mapping field.

7. The current source density imaging system of claim 1, wherein said recording electrodes are placed on a surgical device selected from the group consisting of a laparoscopic device, a catheter, a lead wire, an electrode probe and combinations thereof.

8. The current source density imaging system of claim 1, wherein said timing device comprises a trigger control instrument synchronized to a master clock, said master clock being in synchronous communication with at least one of a field-programmable gate array, programmable logic array or an integrated circuit.

9. The current source density imaging system of claim 1, further comprising a high pass filter and a low pass filter operably connected to said recording electrodes to isolate said acoustoelectric voltage signal detected by said recording electrodes.

10. The current source density imaging system of claim 1, wherein said ultrasound pulser is operable to transmit coded pulse sequences to said ultrasound transducer, said coded pulse sequences comprising chirp coded pulses, Barker coded pulses or Golay coded pulses.

11. A method of mapping and imaging a current source in an electrically active living tissue comprising:
   a. placing a plurality of recording electrodes within a mapping field and substantially near a living tissue having a bioelectric current source, said recording electrodes detecting a voltage signal;
   b. directing an ultrasound beam to at least one position in said bioelectric current source;
   c. transmitting an ultrasound wave to said mapping field;
   d. measuring a voltage signal at said at least one position comprising an acoustoelectric voltage signal produced at a position located at an intersection between a focal zone of said ultrasound beam and said bioelectric current source through said plurality of recording electrodes;
   e. processing said received acoustoelectric voltage signal to derive position data of said bioelectric current source, said data comprising data points, each data point comprising a magnitude of said bioelectric current source sampled at said at least one position relative to said mapping field in said living tissue;
   f. storing said data points in memory;
   g. converting said data points stored in said memory to an image representing a density of current within at least a portion of said mapping field; and
   h. displaying said image on a display.

12. The method according to claim 11, wherein the placing of said plurality of recording electrodes comprises placing the plurality of electrodes adjacent to the living tissue, within the living tissue, in contact with an outside surface of said living tissue or combinations thereof.

13. The method according to claim 11, wherein the living tissue comprises heart muscle, skeletal muscle, brain tissue, nerve tissue, spinal tissue or electrically conductive cells.

14. The method according to claim 11, wherein directing an ultrasound beam comprises aiming at least one ultrasound transducer in acoustic contact with said at least one position and emitting a plurality of ultrasound waves directed to said at least one position in said mapping field, and wherein said ultrasound transducer has a center frequency of about 100 kHz to about 300 MHz.

15. The method according to claim 11, wherein said measuring a voltage signal further comprises:
   a. isolating said acoustoelectric voltage signal from said voltage signal by filtering said voltage signal with an analog signal conditioner;
   b. amplifying said acoustoelectric voltage signal;
   c. sampling said amplified acoustoelectric voltage signal;
   d. digitizing said sampled acoustoelectric voltage signal; and
   e. storing said digitized acoustoelectric voltage signal in memory.

16. The method according to claim 11, wherein said processing said received acoustoelectric voltage signal to derive position data of said bioelectric current source comprises:
   a. assigning each said acoustoelectric voltage signal stored in memory a first and second dimension spatial coordinate determined by known location of said ultrasound beam emitted from an ultrasound transducer;
   b. assigning each said acoustoelectric voltage signal stored in memory a third dimension spatial coordinate determined by the time required for a propagating ultrasound wave to contact said current source;
   c. conditioning said acoustoelectric voltage signal, said conditioning comprising filtering of at least one dimension spatial coordinate;
   d. converting an amplitude of said digitally conditioned acoustoelectric signal into a colored scale for display in at least one of 2-D or 3-D; and
   e. displaying said colored scale on a display.

17. The method according to claim 16, further comprising reconstructing the position of said received acoustoelectric voltage signal from a plurality of recording electrodes by applying a reconstruction algorithm to said digitally conditioned acoustoelectric voltage signal.

18. The method according to claim 11, wherein converting said data points stored in memory further comprises registering said data points automatically with an image produced by at least one of a pulse-echo ultrasound, blood-flow Doppler, X-ray fluoroscopy, magnetic resonance imaging, computer tomography and optical imaging.

19. The method according to claim 18, wherein registering said data points with an image comprises registering said data points with a pulse-echo ultrasound image obtained with the same propagating ultrasound wave that produces said acoustoelectric voltage signal.

20. A method for mapping a current source density in an electrically active living tissue, the method comprising:
   providing a current source mapping device including an ultrasound emitting device producing an ultrasound wave directed to a bioelectric current source, said ultrasound wave producing an acoustoelectric voltage signal at the bioelectric current source, a voltage recording device recording said acoustoelectric voltage signal produced by said bioelectric current source, a voltage processing device operatively connected to said voltage recording device and a display; and
   directing said ultrasound wave to a position in a mapping field containing said bioelectric current source so that upon contact of said bioelectric current source with said ultrasound wave, said acoustoelectric voltage signal is produced in proportion to current density of said bioelectric current source in said living tissue, wherein said voltage processing device processing said acoustoelectric voltage signal into a digitized representation of said current density at said bioelectric current source and displaying said digitized representation of said current density on said display.

* * * * *

UNITED STATES PATENT AND TRADEMARK OFFICE
CERTIFICATE OF CORRECTION

PATENT NO.      : 8,057,390 B2
APPLICATION NO. : 12/019225
DATED           : November 15, 2011
INVENTOR(S)     : Russell S. Witte et al.

It is certified that error appears in the above-identified patent and that said Letters Patent is hereby corrected as shown below:

Column 2, line 36, after "placing" delete "a".

Column 3, line 43, after "mA/cm²" delete ")".

Column 3, line 52, after "illustrating" delete "of".

Column 4, line 14, after "illustrate" delete "a".

Column 8, line 16, "mA/cm2" should be --mA/cm²--.

Column 8, line 17, "mA/cm2" should be --mA/cm²--.

Column 8, line 24, after "such" insert --as--.

Column 8, line 29, "stimulate" should be --stimulating--.

Column 8, line 38, "a ultrasound" should be --an ultrasound--.

Column 8, line 61, after "nerves" insert --,--.

Column 9, line 14, "clock 2230" should be --clock 230--.

Column 9, line 31, "provide" should be --provided--.

Column 10, line 2, "In stiff" should be --In still--.

Column 10, line 52, after "can be" delete "a".

Column 10, line 65, "is there is" should be --there is--.

Column 12, line 32, "IN" should be --In--.

Column 12, line 33, "A method" should be --a method--.

Column 12, line 38, "source." should be --source,--.

Column 12, line 42, "accoustoelectric" should be --acoustoelectric--.

Column 12, line 43, "current source," should be --current source.--.

Column 12, line 57, "(Ultrasound" should be --(ultrasound--.

Column 14, line 66, "(8 mA/cm2)" should be --(8 mA/cm²)--.

Column 15, line 5, "an" should be --a--.

Signed and Sealed this
Twenty-ninth Day of May, 2012

David J. Kappos
*Director of the United States Patent and Trademark Office*

CERTIFICATE OF CORRECTION (continued)
U.S. Pat. No. 8,057,390 B2

Column 15, line 7, after "mA/cm$^2$" insert --.--.

Column 15, line 61, after "can be" delete "been".

Column 17, line 25, "$v_i^{LP}$" should be --$v_i^{LF}$--.

Column 18, line 45, "layer," should be --layer.--.

Column 19, line 18, "db" should be --dB--.

Column 21, line 60, "100 intervals," should be --10° intervals,--.

Column 22, line 53, "(2.2 mm)," should be --(2.2 mm).--.